(12) United States Patent
Acton, III et al.

(10) Patent No.: US 6,525,083 B2
(45) Date of Patent: Feb. 25, 2003

(54) N-SUBSTITUTED INDOLES USEFUL IN THE TREATMENT OF DIABETES

(75) Inventors: John J. Acton, III, Cranford, NJ (US); Regina Marie Black, Cranford, NJ (US); Anthony Brian Jones, Clavering (GB); Harold Blair Wood, Cranford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/912,961

(22) Filed: Jul. 25, 2001

(65) Prior Publication Data

US 2002/0042441 A1 Apr. 11, 2002

Related U.S. Application Data

(60) Provisional application No. 60/220,778, filed on Jul. 25, 2000.

(51) Int. Cl.[7] ............... A61K 31/405; C07D 209/18; C07D 209/22
(52) U.S. Cl. ............... 514/415; 548/510; 548/511
(58) Field of Search ............... 548/510, 511; 514/415

(56) References Cited

U.S. PATENT DOCUMENTS

| | | | |
|---|---|---|---|
| 5,527,819 A | 6/1996 | Williams et al. | |
| 5,532,237 A | 7/1996 | Gallant et al. | |
| 5,686,481 A | * 11/1997 | Elliott et al. | 514/414 |
| 5,728,709 A | 3/1998 | Ikuina et al. | |
| 6,013,648 A | 1/2000 | Rinaldi et al. | |

FOREIGN PATENT DOCUMENTS

| | | |
|---|---|---|
| BE | 692519 | 1/1967 |
| CH | 605742 | 12/1977 |
| EP | 530907 | 3/1993 |
| WO | WO 90/05721 | 5/1990 |
| WO | WO 92/06088 | 4/1992 |
| WO | WO 93/20078 | 10/1993 |
| WO | WO 94/14434 | 7/1994 |
| WO | WO 96/03377 | 2/1996 |
| WO | WO 96/03400 | 2/1996 |
| WO | WO 98/08818 | 3/1998 |
| WO | WO 99/43651 | 9/1999 |
| WO | WO 99/43654 | 9/1999 |
| WO | WO 99/43672 | 9/1999 |
| WO | WO 00/35886 | 6/2000 |

OTHER PUBLICATIONS

C.K. Lau, et al. Adv. Exp. Med. Biol., 1997, pp. 73–78, vol. 407.
Beilstein Data Base—Registration No. 6,243,651.
Beilstein Data Base—Registration No. 6,250,253.

* cited by examiner

*Primary Examiner*—Joseph K. McKane
*Assistant Examiner*—Rebecca Anderson
(74) *Attorney, Agent, or Firm*—James L. McGinnis; Melvin Winokur

(57) ABSTRACT

Certain N-substituted indoles having aryloxyacetic acid, substituents are agonists or partial agonists of PPAR gamma, and are useful in the treatment, control or prevention of non-insulin dependent diabetes mellitus (NIDDM), hyperglycemia, dyslipidemia, hyperlipidemia, hypercholesterolemia, hypertriglyceridemia, atherosclerosis, obesity, vascular restenosis, inflammation, and other PPAR mediated diseases, disorders and conditions.

37 Claims, No Drawings

N-SUBSTITUTED INDOLES USEFUL IN THE TREATMENT OF DIABETES

CROSS REFERENCE TO RELATED APPLICATIONS

This application claims priority from U.S. Provisional Application No. 60/220,778, filed on Jul. 25, 2000, which is incorporated by reference into this application in its entirety.

FIELD OF THE INVENTION

The instant invention is concerned with N-substituted indoles having aryloxyalkanoic acid substituents, and pharmaceutically acceptable salts and prodrugs thereof, which are useful as therapeutic compounds, particularly in the treatment of Type 2 diabetes mellitus, often referred to as non-insulin dependent diabetes (NIDDM), of conditions that are often associated with this disease, and of lipid disorders.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide), which stimulate the pancreatic β-cells to secrete more insulin, and/or by injection of insulin after the response to sulfonylureas fails, will result in high enough insulin concentrations to stimulate the very insulin-resistant tissues. However, dangerously low levels of plasma glucose can result from these last two treatments, and increasing insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea, respectively.

The glitazones (i.e. 5-benzylthiazolidine-2,4-diones) are a more recently described class of compounds with potential for a novel mode of action in preventing or ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia.

Disorders of lipid metabolism or dyslipidemias include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Cholesterol is mostly carried in Low Density Lipoproteins (LDL), and this component is commonly known as the "bad" cholesterol because it has been shown that elevations in LDL-cholesterol correlate closely to the risk of coronary heart disease. A smaller component of cholesterol is carried in the High Density Lipoproteins and is commonly known as the "good" cholesterol. In fact, it is known that the primary function of HDL is to accept cholesterol deposited in the arterial wall and to transport it back to the liver for disposal through the intestine. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91 (1979). An example of an HDL raising agent is nicotinic acid, a drug with limited utility because doses that achieve HDL raising are associated with undesirable effects, such as flushing.

Dyslipidemias were originally classified by Fredrickson according to the combination of alterations mentioned above. The Fredrickson classification includes 6 phenotypes (i.e., I, IIa, IIb, III, IV and V) with the most common being the isolated hypercholesterolemia (or type IIa) which is usually accompained by elevated concentrations of total and LDL cholesterol. The initial treatment for hypercholesterolemia is often to modify the diet to one low in fat and cholesterol, coupled with appropriate physical exercise, followed by drug therapy when LDL-lowering goals are not met by diet and exercise alone A second common form of dyslipidemia is the mixed or combined hyperlipidemia or type IIb and III of the Fredrickson classification. This dyslipidemia is often prevalent in patients with type 2 diabetes, obesity and the metabolic syndrome. In this dyslipidemia there are modest elevations of LDL-cholesterol, accompanied by more pronounced elevations of small dense LDL-cholesterol particles, VLDL and/or IDL (i.e., triglyceride rich lipoproteins), and total triglycerides. In addition, concentrations of HDL are often low.

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of lipid modulating drugs, herbicides and phthalate plasticizers. Peroxisome proliferation is also triggered by dietary or physiological factors such as a high-fat diet and cold acclimatization.

Three sub-types of peroxisome proliferator activated receptor (PPAR) have been discovered and described; they are peroxisome proliferator activated receptor alpha (PPARα), peroxisome proliferator activated receptor gamma (PPARγ) and peroxisome proliferator activated receptor delta (PPARδ). Identification of PPARα, a member of the nuclear hormone receptor superfamily activated by peroxisome proliferators, has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also associated with the activity of fibrates and fatty acids in rodents and humans. Fibric acid derivatives such as clofibrate, fenofibrate, benzafibrate, ciprofibrate, beclofibrate and etofibrate, as well as gemfibrozil, each of which are PPARα ligands and/or activators, produce a substantial reduction in plasma triglycerides as well as some increase in HDL. The effects on LDL cholesterol are inconsistent and might depend upon the compound and/or the dyslipidemic phenotype. For these reasons, this class of compounds has been primarily used to treat hypertriglyceridemia (i.e, Fredrickson Type IV and V) and/or mixed hyperlipidemia.

The PPARγ receptor subtypes are involved in activating the program of adipocyte differentiation and are not involved in stimulating peroxisome proliferation in the liver. There are two known protein isoforms of PPARγ PPARγ1 and PPARγ2 which differ only in that PPARγ2 contains an additional 28 amino acids present at the amino terminus. The DNA sequences for the human isotypes are described in Elbrecht, et al., BBRC 224;431–437 (1996). In mice, PPARγ2 is expressed specifically in fat cells. Tontonoz et al., Cell 79: 1147–1156 (1994) provide evidence to show that one physiological role of PPARγ2 is to induce adipocyte differentiation. As with other members of the nuclear hormone receptor superfamily, PPARγ2 regulates the expression of genes through interaction with other proteins and binding to hormone response elements, for example in the 5' flanking regions of responsive genes. An example of a PPARγ2 responsive gene is the tissue-specific adipocyte P2 gene. Although peroxisome proliferators, including the fibrates and fatty acids, activate the transcriptional activity of PPAR's, only prostaglandin $J_2$ derivatives have been identified as potential natural ligands of the PPARγ subtype, which also binds thiazolidinedione antidiabetic agents with high affinity.

The human nuclear receptor gene PPARδ (hPPARδ) has been cloned from a human osteosarcoma cell cDNA library and is fully described in A. Schmidt et al., *Molecular Endocrinology*, 6:1634–1641 (1992). It should be noted that PPARδ is also referred to in the literature as PPARβ and as NUC1, and each of these names refers to the same receptor; in Schmidt et al. the receptor is referred to as NUC1.

In WO96/01430, a human PPAR subtype, hNUC1B, is disclosed. The amino acid sequence of hNUC1B differs from human PPARδ (referred to therein as hNUC1) by one amino acid, i.e., alanine at position 292. Based on in vivo experiments described therein, the authors suggest that hNUC1B protein represses hPPARα and thyroid hormone receptor protein activity.

It has been disclosed in WO97/28149 that agonists of PPARδ are useful in raising HDL plasma levels. WO97/27857, 97/28115, 97/28137 and 97/27847 disclose compounds that are useful as antidiabetic, antiobesity, antiartherosclerosis and antihyperlipidemic agents, and which may exert their effect through activation of PPARs.

It is generally believed that glitazones exert their effects by binding to the peroxisome proliferator activated receptor (PPAR) family of receptors, controlling certain transcription elements having to do with the biological entities listed above. See Hulin et al., Current Pharm. Design (1996) 2, 85–102. In particular, PPARγ has been implicated as the major molecular target for the glitazone class of insulin sensitizers.

A number of glitazones that are PPAR agonists have been approved for use in the treatment of diabetes. These are troglitazone, rosiglitazone and pioglitazone, all of which are primarily or exclusively PPARγ agonists. Although glitazones are beneficial in the treatment of NIDDM, there have been some serious adverse events associated with the use of the compounds. The most serious of these has been liver toxicity, which has resulted in a number of deaths. The most serious problems have occurred using troglitazone, which was recently withdrawn from the market because of toxicity concerns.

In addition to potential hepatotoxicity, there are several shortcomings associated with the glitazones: (1) Monotherapy for NIDDM produces modest efficacy—reductions in average plasma glucose of ≈20% or a decline from ≈9.0% to ≈8.0% in HemoglobinA1C. (2) There is room for improvement in lipid effects; troglitazone causes a slight increase in LDL cholesterol, and triglyceride lowering is modest relative to the effect of fibrates; results reported to date with rosiglitazone suggest no effect on triglycerides and a possible net increase in the LDL:HDL ratio. Currently available data on pioglitazone appear to indicate that it lowers triglycerides modestly and may also have a neutral or positive effect on LDL vs. HDL (i.e. slight HDL raising with no effect on LDL). (3) All three glitazones have been associated with significant weight gain as well as other AE's (mild edema and mild anemia). These shortcomings provide an opportunity to develop better insulin sensitizers for Type 2 diabetes which function via similar mechanism(s) of action.

Because of the problems that have occurred with the glitazones, researchers in a number of laboratories have been investigating classes of PPAR agonists that are not glitazones and do not contain 1,3-thiazolidinedione moieties, but that modulate the three known PPAR subtypes, in concert or in isolation, to varying degrees (as measured by intrinsic potency, maximal extent of functional reponse or spectrum of changes in gene expression). Such classes of compounds are expected to be useful in the treatment of diabetes and associated conditions, dyslipidemias and associated conditions and several other indications and may be free of some of the side effects that have been found in many of the glitazones.

SUMMARY OF THE INVENTION

The class of compounds described herein is a new class of PPAR agonists that do not contain a 1,3-thiazolidinedione moiety and therefore are not glitazones. The class of compounds includes compounds that are primarily PPARγ agonists and PPARγ partial agonists. Some compounds may also have PPARα activity in addition to the PPARγ activity, so that the compounds are mixed PPARα/γ agonists. These compounds are useful in the treatment, control and/or prevention of diabetes, hyperglycemia, and insulin resistance. The compounds of the invention exhibit reduced side effects relating to body and heart weight gain in preclinical animal studies compared with other PPARγ compounds including rosiglitazone.

The compounds may also be useful in the treatment of mixed or diabetic dyslipidemia and other lipid disorders (including isolated hypercholesterolemia as manifested by elevations in LDL-C and/or non-HDL-C and/or hyperapoBliproteinemia, hypertriglyceridemia and/or increase in triglyceride-rich-lipoproteins, or low HDL cholesterol concentrations), atherosclerosis, obesity, vascular restenosis, inflammatory conditions, neoplastic conditions, psoriasis, polycystic ovary syndrome and other PPAR mediated diseases, disorders and conditions.

The present invention is directed to compounds of formula I:

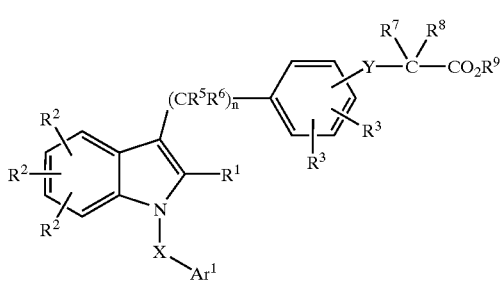

wherein:
- $R^1$ is methyl, optionally substituted with 1–3 F;
- $R^2$, $R^3$ and $R^4$ are each independently selected from the group consisting of H, halogen, $C_1$–$C_6$ alkyl, $C_2$–$C_6$ alkenyl, $C_2$–$C_6$ alkynyl, $C_3$–$C_8$ cycloalkyl, aryl, $OC_1$–$C_6$ alkyl, $OC_2$–$C_6$ alkenyl, $OC_2$–$C_6$ alkynyl, O-aryl, OH, $SC_1$–$C_6$ alkyl, $SC_2$–$C_6$ alkenyl, $SC_2$–$C_6$ alkynyl, $SO_2C_1$–$C_6$ alkyl, $SO_2C_2$–$C_6$ alkenyl, $SO_2C_2$–$C_6$ alkynyl, $OCON(R_5)_2$, $OCO(C_1$–$C_6$-alkyl) and CN, wherein all instances of alkyl, alkenyl and alkynyl are optionally linear or branched and all instances of alkyl, alkenyl, alkynyl, cycloalkyl and aryl are optionally substituted with 1–5 substituents independently selected from the group consisting of halogen, aryl, O-aryl and OMe;
- $R^5$ and $R^6$ are, at each occurrence, independently selected from the group consisting of H, F, OH and $C_1$–$C_5$ alkyl, and $R^5$ and $R^6$ groups that are on the same carbon atom optionally may be joined to form a $C_3$–$C_6$ cycloalkyl group;
- $R^7$ and $R^8$ are each independently selected from the group consisting of H, F, and $C_{1-5}$ alkyl, or $R^7$ and $R^8$ optionally may be joined to form a $C_3$–$C_6$ cycloalkyl group;
- $R^9$ is selected from the group consisting of H and $C_1$–$C_5$ alkyl, said alkyl being optionally linear or branched;
- $Ar^1$ is phenyl, 1-naphthyl, 2-naphthyl, pyridyl or quinolyl wherein $Ar^1$ is substituted with 1–3 groups independently selected from $R^4$;
- X is selected from the group consisting of C=O, $S(O)_2$, $CH_2$, $CH(CH_3)$, $C(CH_3)_2$, $CF_2$, and cyclopropylidene;
- Y is O or S; and
- n is 0–5;

and pharmaceutically acceptable salts and prodrugs thereof.

The present compounds are effective in lowering glucose, lipids, and insulin in diabetic animals and lipids in non-diabetic animals. The compounds are expected to be efficacious in the treatment, control and/or prevention of non-insulin dependent diabetes mellitus (NIDDM) in humans and in the treatment, control, and/or prevention of conditions associated with NIDDM, including hyperlipidemia, dyslipidemia, obesity, hypercholesterolemia, hypertrigyceridemia, atherosclerosis, vascular restenosis, inflammatory conditions, neoplastic conditions, and other PPAR mediated diseases, disorders and conditions.

DETAILED DESCRIPTION OF THE INVENTION

The invention has numerous embodiments. It provides compounds of formula I, including pharmaceutically acceptable salts of these compounds, prodrugs of these compounds, and pharmaceutical compositions comprising any of the compounds described and a pharmaceutically acceptable carrier.

In one embodiment, in compounds having the formula I, $R^1$ is $CH_3$.

In another embodiment of compounds having the formula I, $R^1$ is $CH_3$;
- $R^2$, $R^3$, and $R^4$ are each independently selected from the group consisting of H, halogen, $C_1$–$C_6$ alkyl, $C_2$–$C_6$ alkenyl, $C_2$–$C_6$ alkynyl, $C_3$–$C_8$ cycloalkyl, aryl, $OC_1$–$C_6$ alkyl, $OC_2$–$C_6$ alkenyl, $OC_2$–$C_6$ alkynyl, O-aryl, OH, $SC_1$–$C_6$ alkyl, $SC_2$–$C_6$ alkenyl, $SC_2$–$C_6$ alkynyl, $OCON(R_5)_2$, $OCO(C_1$–$C_6$-alkyl) and CN, wherein all instances of alkyl, alkenyl and alkynyl are optionally linear or branched and all instances of alkyl, alkenyl, alkynyl, cycloalkyl and aryl are optionally substituted with 1–5 substituents independently selected from the group consisting of halogen, aryl, O-aryl and OMe; and
- X is selected from the group consisting of C=O, $CH_2$, $CH(CH_3)$, $C(CH_3)_2$, $CF_2$, and cyclopropylidene.

In another embodiment, in compounds having the formula I, $R^2$, $R^3$, and $R^4$ are each independently selected from the group consisting of H, $OCH_3$, $OCF_3$, F, Cl and $CH_3$, where $CH_3$ is optionally substituted with 1–3 groups independently selected from F, Cl, and $OCH_3$. In more specific embodiments, R2, R3, and R4 are each independently selected from the group consisting of H, $OCH_3$, $OCF_3$, and Cl.

In another group of compounds having the formula I, $R^5$ and $R^6$ are H.

In another group of compounds having the formula I, $R^7$ and $R^8$ are each independently $CH_3$ or H.

In preferred groups of compounds having the formula I, $R^9$ is H.

In other compounds having formula I, X is C=O.

In other compounds having formula I, Y is O.

In another group of compounds having formula I, n is 0, 1, or 2. In a more specific subset of this group of compounds, n is 1.

Another group of compounds having formula I includes compounds in which $Ar^1$ is phenyl, 1-naphthyl or 2-naphthyl. A subset of this group of compounds includes compounds in which $Ar^1$ is phenyl or 2-naphthyl. In either case, $Ar^1$ is substituted with 1–3 groups independently selected from $R^4$.

In preferred groups of compounds, aryl substituents are phenyl groups.

A preferred set of compounds having formula I has the following substituents:

$R^1$ is $CH_3$;
$R^2$ is selected from the group consisting of H, $OCH_3$, and $OCF_3$;
$R^3$, $R^5$, $R^6$, and $R^9$ are H;
$R^4$ is selected from the group consisting of H, Cl, and $OCH_3$;
$R^7$ and $R^8$ are each independently selected from the group consisting of H and $CH_3$;
X is C=O;
Y is O;
and n is 1.

Specific examples of compounds of this invention are provided as Examples 1–31, named below:

EXAMPLE 1
(2S)-2-(3-{[1-(4-Methoxybenzoyl)-2-methyl-5-(trifluoromethoxy)-1H-indol-3-yl]methyl}phenoxy) propanoic acid EXAMPLE 2
2-(2-{[1-(4-Chlorobenzoyl)-2-methyl-5-(methoxy)-1H-indol-3-yl]methyl}phenoxy)acetic acid EXAMPLE 3
2-(3-{[1-(4-Chlorobenzoyl)-2-Methyl-5-(methoxy)-1H-indol-3-yl]methyl}phenoxy)acetic acid EXAMPLE 4
2-(4-{[1-(4-Chlorobenzoyl)-2-methyl-5-(methoxy)-1H-indol-3-yl]methyl}phenoxy)acetic acid EXAMPLE 5
2-(2-{[1-(4-Chlorobenzoyl)-2-methyl-5-(methoxy)-1H-indol-3-yl]methyl}phenoxy)propanoic acid EXAMPLE 6
2-(3-{[1-(4-Chlorobenzoyl)-2-methyl-5-(methoxy)-1H-indol-3-yl]methyl}phenoxy)propanoic acid EXAMPLE 7
2-(4-{[1-(4-Chlorobenzoyl)-2-methyl-5-(methoxy)-1H-indol-3-yl]methyl}phenoxy)propanoic acid EXAMPLE 8
2-(2-{[1-(4-Chlorobenzoyl)-2-methyl-5-(methoxy)-1H-indol-3-yl]methyl}phenoxy)-2-methylpropanoic acid EXAMPLE 9
2-(3-{[1-(4-Chlorobenzoyl)-2-methyl-5-(methoxy)-1H-indol-3-yl]methyl}phenoxy)-2-methylpropanoic acid EXAMPLE 10
2-(4-{[1-(4-Chlorobenzoyl)-2-methyl-5-(methoxy)-1H-indol-3-yl]methyl}phenoxy)-2-methylpropanoic acid EXAMPLE 11
2-(2-{[1-(4-Methoxybenzoyl)-2-methyl-5-(trifluoromethoxy)-1H-indol-3-yl]methyl}phenoxy) acetic acid EXAMPLE 12
2-(3-{[1-(4-Methoxybenzoyl)-2-Methyl-5-(trifluoromethoxy)-1H-indol-3-yl]methyl}phenoxy) acetic acid EXAMPLE 13
2-(2-{[1-(4-methoxybenzoyl)-2-Methyl-5-(trifluoromethoxy)-1H-indol-3-yl]methyl}phenoxy) propanoic acid EXAMPLE 14
2-(2-{[1-(2-naphthoyl)-2-Methyl-5-(trifluoromethoxy)-1H-indol-3-yl]methyl}phenoxy) propanoic acid EXAMPLE 15
(2R)-2-(2{[1-(4-methoxybenzoyl)-2-Methyl-5-(trifluoromethoxy)-1H-indol-3-yl]methyl}phenoxy) propanoic acid EXAMPLE 16
(2S)-2-(2-{[1-(4-Methoxybenzoyl)-2-methyl-5-(trifluoromethoxy)-1H-indol-3-yl]methyl}phenoxy) propanoic acid EXAMPLE 17
2-(3-{[1-(4-Methoxybenzoyl)-2-methyl-5-(trifluoromethoxy)-1H-indol-3-yl]methyl}phenoxy) propanoic acid EXAMPLE 18
2-(3-{[1-(2-Naphthoyl)-2-methyl-5-(trifluoromethoxy)-1H-indol-3-yl]methyl}phenoxy) propanoic acid EXAMPLE 19
2-(3-{[1-(4-Chlorobenzoyl)-2-methyl-5-(trifluoromethoxy)-1H-indol-3-yl]methyl}phenoxy) propanoic acid EXAMPLE 20
2-(3-{[1-(2,4-Dichlorobenzoyl)-2-methyl-5-(trifluoromethoxy)-1H-indol-3-yl]methyl}phenoxy) propanoic acid EXAMPLE 21
(2R)-2-(3-{[1-(4-Methoxybenzoyl)-2-methyl-5-(trifluoromethoxy)-1H-indol-3-yl]methyl}phenoxy) propanoic acid EXAMPLE 22
(2R)-2-(3-{[1-(2-Naphthoyl)-2-methyl-5-(trifluoromethoxy)-1H-indol-3-yl]methyl}phenoxy) propanoic acid EXAMPLE 23
(2S)-2-(3-{[1-(2-Naphthoyl)-2-methyl-5-(trifluoromethoxy)-1H-indol-3yl]methyl}phenoxy) propanoic acid EXAMPLE 24
2-(2-{[1-(4-Methoxybenzoyl)-2-methyl-5-(trifluoromethoxy)-1H-indol-3-yl]methyl}phenoxy)-2-methylpropanoic acid EXAMPLE 25
2-(3-{[1-(4-Methoxybenzoyl)-2-methyl-5-(trifluoromethoxy)-1H-indol-3-yl]methyl}phenoxy)-2-methylpropanoic acid EXAMPLE 26
2-(2-{[1-(2-Naphthoyl)-2-methyl-5-(trifluoromethoxy)-1H-indol-3-yl]methyl}phenoxy)-2-methylpropanoic acid EXAMPLE 27
2-(3-{[1-(2-Naphthoyl)-2-methyl-5-(trifluoromethoxy)-1H-indol-3-yl]methyl}phenoxy)-2-methylpropanoic acid EXAMPLE 28
(2R)-2-(3-{2-[1-(4-Methoxybenzoyl)-2-methyl-5-(trifluoromethoxy)-1H-indol-3-yl]ethyl}phenoxy) propionic acid EXAMPLE 29
(2S)-2-{3-[1-(4-methoxybenzoyl)-2-methyl-5-(trifluoromethoxy)-1H-indol-3-yl] phenoxy}propionic acid EXAMPLE 30
(2S)-2-(3-{1-{1-(4-Methoxybenzoyl)-2-methyl-5-(trifluoromethoxy)-1H-indol-3-yl] cyclopropyl}phenoxy)propanoic acid

EXAMPLE 31
2-{3-[1-(4-Methoxybenzoyl)-2-methyl-5-(trifluoromethoxy)-1H-indol-3-yl]phenoxy}-2-methylpropanoic acid.
The structures of these specific compounds are shown in the following Table of Examples:
TABLE OF EXAMPLES
| | TABLE OF EXAMPLES |
|---|---|
| Example 1 | 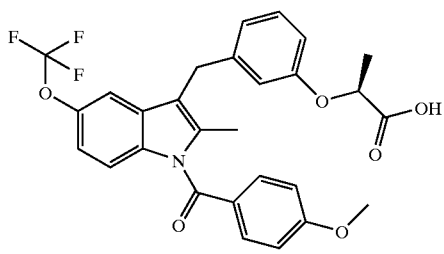 |
| Example 2 | 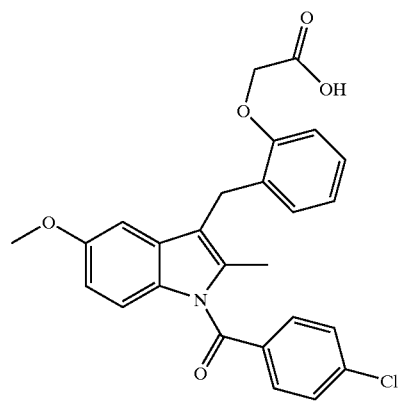 |
| Example 3 | 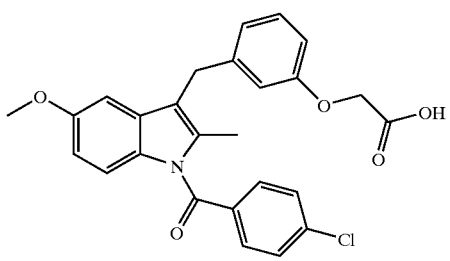 |
| Example 4 | 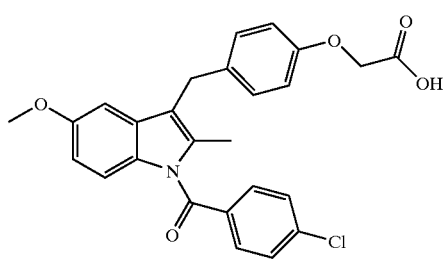 |
| Example 5 | 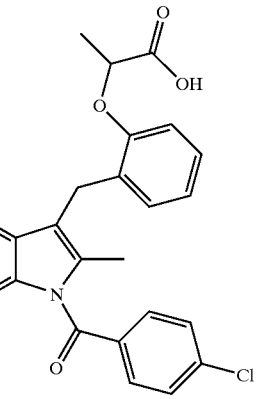 |
| Example 6 | 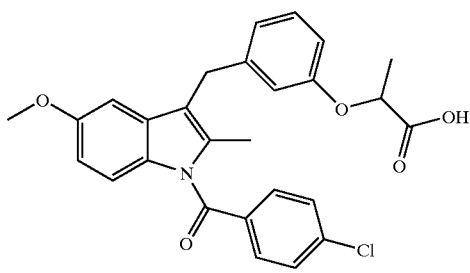 |
| Example 7 | 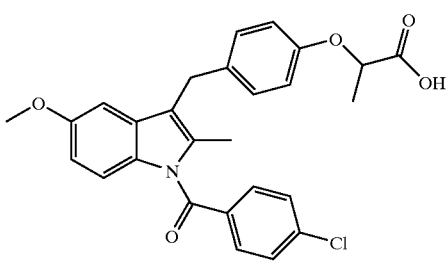 |
| Example 8 | 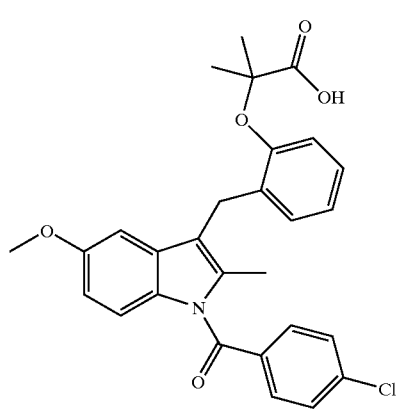 |

-continued
TABLE OF EXAMPLES
Example 9
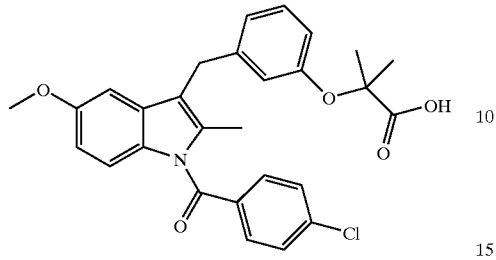
Example 10
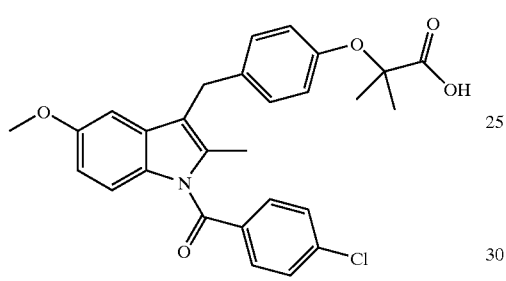
Example 11
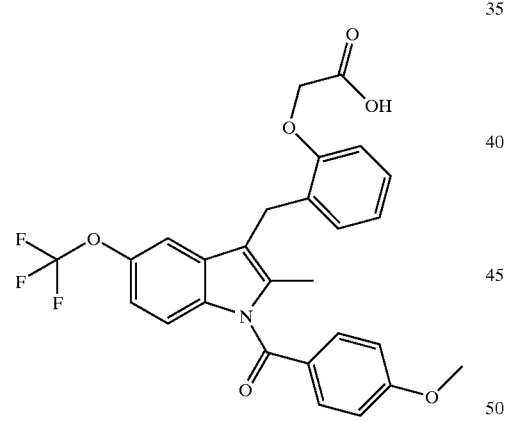
Example 12
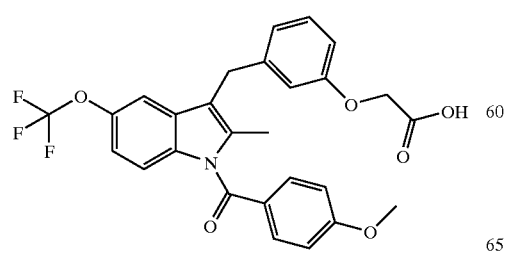
-continued
TABLE OF EXAMPLES
Example 13
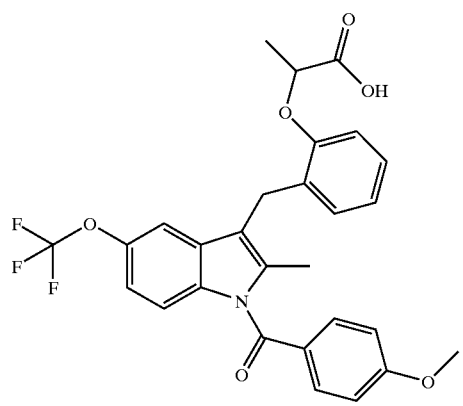
Example 14
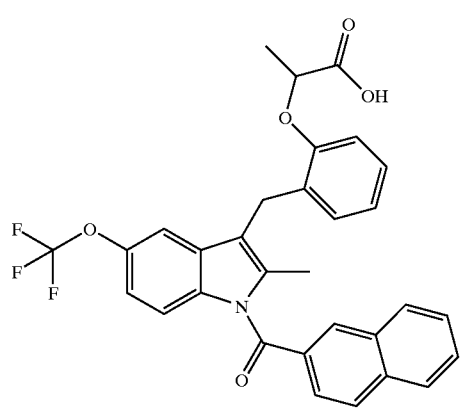
Example 15
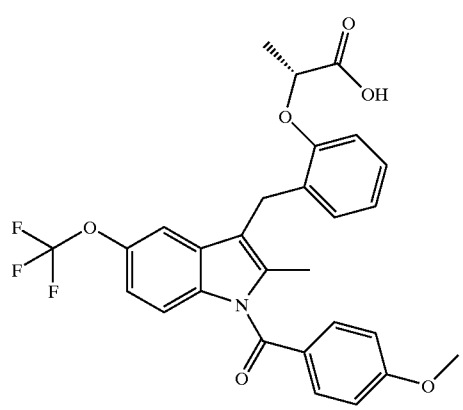
Example 16
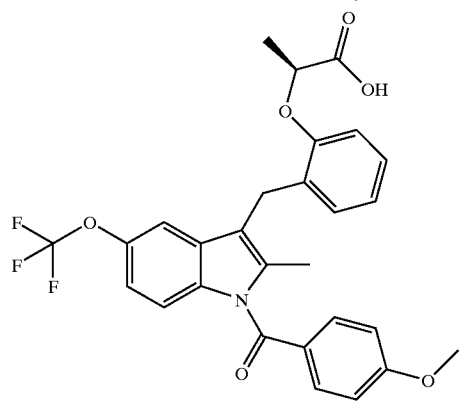

-continued
TABLE OF EXAMPLES
Example 17
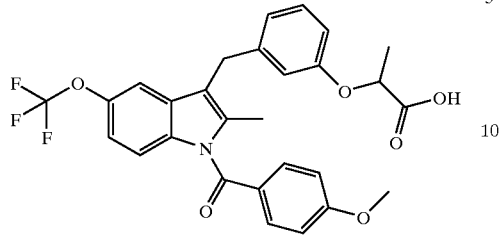
Example 18
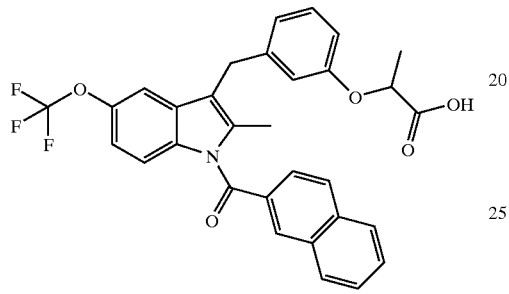
Example 19
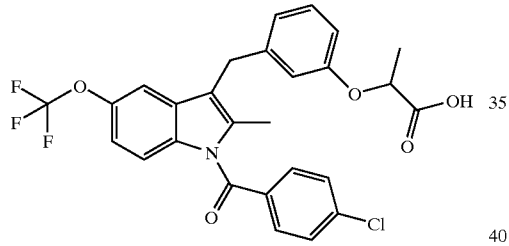
Example 20
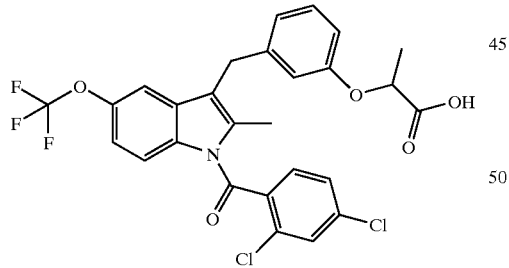
Example 21
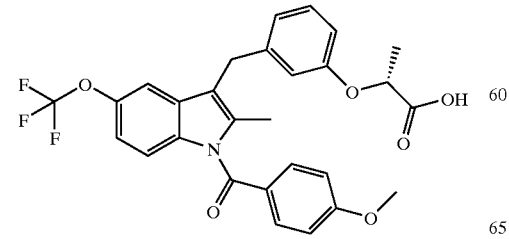
-continued
TABLE OF EXAMPLES
Example 22
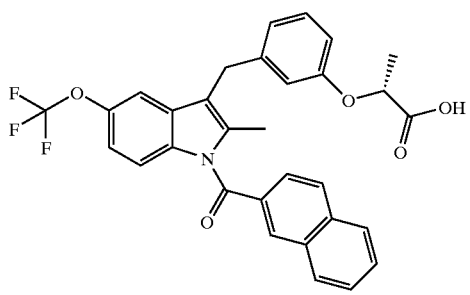
Example 23
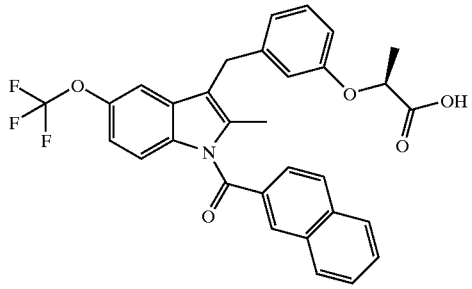
Example 24
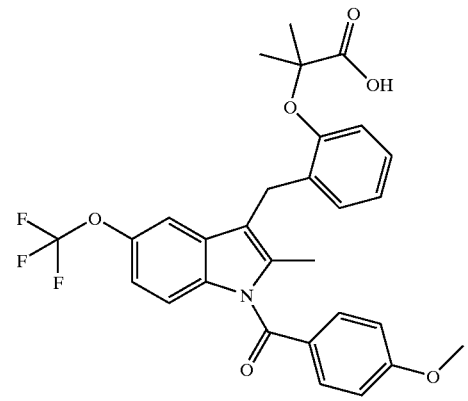
Example 25
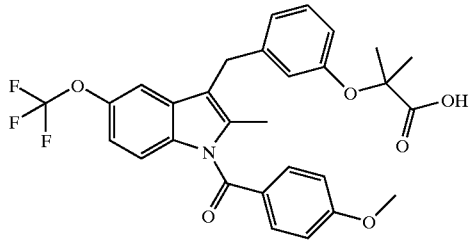

TABLE OF EXAMPLES

Example 26

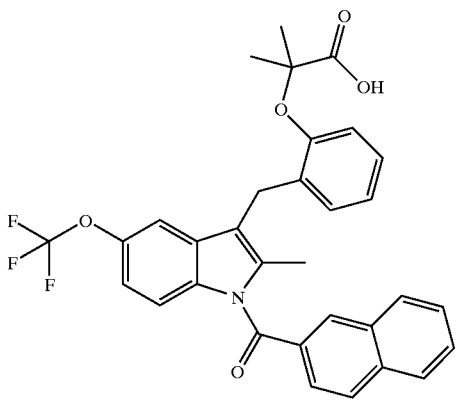

Example 27

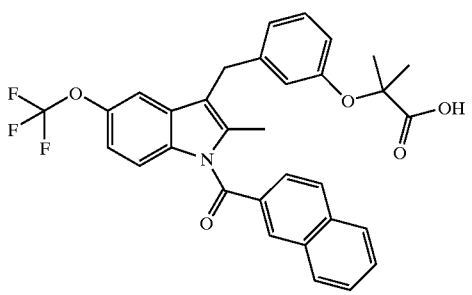

Example 28

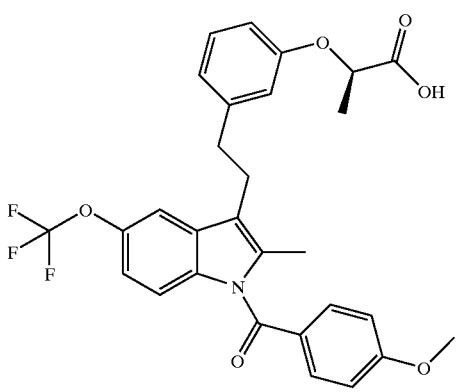

Example 29

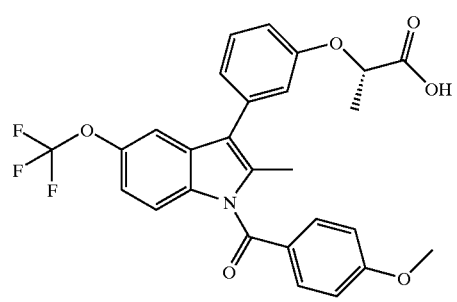

TABLE OF EXAMPLES

Example 30

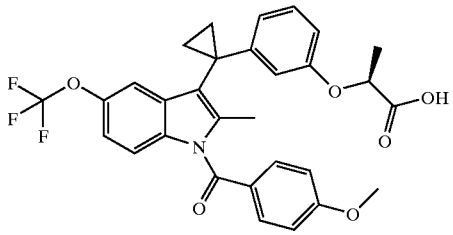

Example 31

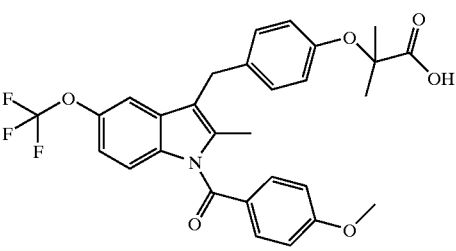

The compounds as defined above are useful in the following methods of treating, controlling, and preventing diseases, as well as other diseases not listed below:

(1) a method for treating, controlling or preventing diabetes mellitus, and particularly non-insulin dependent diabetes mellitus, in a mammalian patient in need of such treatment which comprises administering to the patient a therapeutically effective amount of a compound of Formula I;

(2) a method for treating, controlling, or preventing hyperglycemia in a mammalian patient in need of such treatment which comprises administering to the patient a therapeutically effective amount of a compound of Formula I;

(3) a method for treating, controlling, or preventing lipid disorders, hyperlipidemia, or low HDL in a mammalian patient in need of such treatment which comprises administering to the patient a therapeutically effective amount of a compound of Formula I;

(4) a method for treating, controlling, or preventing obesity in a mammalian patient in need of such treatment which comprises administering to the patient a therapeutically effective amount of a compound of Formula I;

(5) a method for treating, controlling, or preventing hypercholesterolemia in a mammalian patient in need of such treatment which comprises administering to the patient a therapeutically effective amount of a compound of Formula I;

(6) a method for treating, controlling, or preventing hypertriglyceridemia in a mammalian patient in need of such treatment which comprises administering to the patient a therapeutically effective amount of a compound of Formula I;

(7) a method for treating, controlling, or preventing dyslipidemia, including low HDL cholesterol, in a mammalian patient in need of such treatment which comprises administering to the patient a therapeutically effective amount of a compound of Formula I;

(8) a method for treating, controlling, or preventing atherosclerosis in a mammalian patient in need of such treatment which comprises administering to the patient a therapeutically effective amount of a compound of Formula I. It is understood that the sequellae of atherosclerosis (angina, claudication, heart attack, stroke, etc.) are thereby treated.

Definitions

"Ac" is acetyl, which is $CH_3C(O)$—.

"Alkyl", as well as other groups having the prefix "alk", such as alkoxy or alkanoyl, means carbon chains which may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each having from 3 to 10 carbon atoms, unless otherwise stated. The term also includes a monocyclic ring fused to an aryl group in which the point of attachment is on the non-aromatic portion. Examples of cycloalkyl include cyclopropyl, cyclopentyl, cyclohexyl, cycloheptyl, and the like.

"Aryl" (and "arylene") when used to describe a substituent or group in a structure means a monocyclic, bicyclic or tricyclic compound in which all the rings are aromatic and which contains only carbon ring atoms. The term "aryl" can also refer to an aryl group fused to a monocyclic cycloalkyl or monocyclic heterocycle in which the point(s) of attachment is on the aromatic portion. "Heterocyclyl," "heterocycle," and "heterocyclic" means a fully or partially saturated monocyclic, bicyclic or tricyclic ring system containing at least one heteroatom selected from N, S and O, each of said rings having from 3 to 10 atoms. Examples of aryl substituents include phenyl and naphthyl. Aryl rings fused to cycloalkyls are found in indanyl, indenyl, and tetrahydronaphthyl. Examples of aryl fused to heterocyclic groups are found in 2,3-dihydrobenzofuranyl, benzopyranyl, 1,4-benzodioxanyl, and the like. Examples of heterocycles include tetrahydrofuran, piperazine, and morpholine. Preferred aryl groups are phenyl rings.

"Heteroaryl" (and heteroarylene) means a mono-, bi- or tricyclic aromatic ring containing at least one ring heteroatom selected from N, O and S (including SO and $SO_2$), with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b) pyridyl, quinolyl, indolyl, isoquinolyl, dibenzofuran and the like.

"Halogen" includes fluorine, chlorine, bromine and iodine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers—Diastereomers—Geometric Isomers—Tautomers

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein may contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form, known as keto-enol tautomers. The individual tautomers as well as mixtures thereof are encompassed with compounds of Formula I.

Compounds of the Formula I having two asymmetric centers may be separated into diastereoisomeric pairs of enantiomers by, for example, fractional crystallization from a suitable solvent, for example methanol or ethyl acetate or a mixture thereof. The pair of enantiomers thus obtained, and enantiomeric pairs in general, may be separated into individual stereoisomers by conventional means, for example by the use of an optically active acid or base as a resolving agent or chiral separation columns.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylendediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites of other compounds, where the metabolites themselves fall within the scope of the claims herein, are also claimed. Prodrugs, which are compounds that are converted to the claimed compounds as they are being administered to a patient or after they have been administered to a patient, are also claimed as part of this invention. A non-limiting example of a prodrug of the carboxylic acids of this invention would be an ester of the carboxylic acid group, for example a $C_1$ to $C_6$ ester, which may be linear or branched, which metabolizes to a compound claimed herein. An ester which has functionality that makes it more easily hydrolyzed after administration to a patient may also be a prodrug.

Prodrugs of the class of compounds of this invention may be described as compounds having the Formula I, wherein $R^9$ is now defined as a group that is easily removed under physiological conditions during or after administration to a mammalian patient to yield a compound having Formula I, where $R^9$ is H, or the carboxylate anion thereof (in solution), or a pharmaceutically acceptable salt thereof, where the substituents and groups and values of n are as defined above for compounds having Formula I.

Examples of prodrugs of Formula I include compounds in which $OR^9$ of the $CO_2R^9$ group is selected from the group consisting of —$OR^{10}$, —$OCH_2OR^{10}$, —$OCH(CH_3)OR^{10}$, —$OCH_2OC(O)R^{10}$, —$OCH(CH_3)OC(O)R^{10}$, —$OCH_2OC(O)OR^{10}$, —$OCH(CH_3)OC(O)OR^{10}$, —$NR^{11}R^{11}$, and —$ONR^{11}R^{11}$, where each $R^{10}$ is independently selected from $C_{1-6}$ alkyl optionally substituted with one or two groups selected from —$CO_2H$, —$CONH_2$, —$NH_2$, —$OH$, —$OAc$, $NHAc$, and phenyl; and wherein each $R^{11}$ is independently selected from H and $R^{10}$. Compounds having Formula I, where $R^9$ has the chemical structure described above, are described as prodrugs. However, regardless of whether they are active as prodrugs, yielding compounds or salts of Formula I, or whether they have a different means of exhibiting pharmaceutical activity, such compounds are included in this invention. Such compounds are claimed herein, regardless of the mechanism leading to their activity.

Utilities

Compounds of the present invention are potent ligands with agonist or partial agonist activity on the various peroxisome proliferator activator receptor subtypes, particularly PPARγ. The compounds may also be ligands or agonists of the PPARα subtype as well, resulting in mixed PPARα/γ agonism or in agonism of mainly the PPARα subtype. These compounds are useful in treating, controlling or preventing diseases, disorders or conditions, wherein the treatment is mediated by the activation of an individual PPAR subtype (γ or α) or a combination of PPAR subtypes (e.g. α/γ), and particularly the PPARγ subtype. One aspect of the present invention provides a method for the treatment, control or prevention of such diseases, disorders, or conditions in a mammal which comprises administering to such mammal a therapeutically effective amount of a compound of Formula I. Compounds of the present invention may be useful in treating, controlling or preventing many PPAR mediated diseases and conditions, including, but are not limited to, (1) diabetes mellitus, and especially non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29) high blood pressure, (30) Syndrome X, (31) ovarian hyperandrogenism (polycystic ovarian syndrome), and other disorders where insulin resistance is a component.

Another aspect of the invention provides a method for the treatment, control, or prevention of hypercholesterolemia, atherosclerosis, low HDL levels, high LDL levels, hyperlipidemia, hypertriglyceridemia, and/or dyslipidemia, which comprises administering to a mammal in need of such treatment a therapeutically effective amount of a PPAR agonist or partial agonist having formula I. The PPAR agonist may be used alone or advantageously may be administered with a cholesterol biosynthesis inhibitor, particularly an HMG-CoA reductase inhibitor such as lovastatin, simvastatin, pravastatin, fluvastatin, atorvastatin, rivastatin, itavastatin, or ZD-4522. The PPAR agonist may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), and with niacin, bile acid sequestrants, microsomal triglyceride transport inhibitors, and bile acid reuptake inhibitors. These combination treatments may also be effective for the treatment, control or prevention of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a PPAR agonist, which may be a PPARα agonist, a PPARγ agonist, or a PPARα/γ dual agonist. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or prodrug thereof as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment, prevention, suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) (i) other PPAR agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin; (iii) protein tyrosine phosphatase-1B (PTP-1B) inhibitors, and (iv) dipeptidyl peptidase IV (DP-IV) inhibitors;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin, pravastatin, fluvastatin, atorvastatin, rivastatin, itavastatin, ZD-4522 and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) PPARα/γ dual agonists, such as KRP-297, (vi) inhibitors of cholesterol absorption, such as for example beta-sitosterol, (vii) acyl CoA:cholesterol acyltransferase inhibitors, such as for example avasimibe, and (viii) anti-oxidants, such as probucol;

(f) PPARδ agonists such as those disclosed in WO97/28149;

(g) antiobesity compounds such as fenfluramine, dexfenfluramine, phentiramine, sulbitramine, orlistat, neuropeptide Y5 inhibitors, and $\beta_3$ adrenergic receptor agonists;

(h) an ileal bile acid transporter inhibitor; and (i) agents intended for use in inflammatory conditions such as aspirin, non-steroidal anti-inflammatory drugs, glucocorticoids, azulfidine, and cyclo-oxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

Biological Assays

A) PPAR Binding Assays

For preparation of recombinant human PPARγ, PPARδ, and PPARα: Human PPARγ$_2$, human PPARδ and human PPARα were expressed as gst-fusion proteins in $E.$ $coli$. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). $E.$ $coli$ containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C. For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$]AD5075, (21 Ci/mmole), ±test compound as described in Berger et al (Novel peroxisome proliferator-activated receptor (PPARγ) and PPARδ ligands produce distinct biological effects. J. Biol. Chem. (1999), 274: 6718–6725. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]L-783483, (17 Ci/mmole), ±test compound as described in Berger et al (Novel peroxisome proliferator-activated receptorγ (PPARγ) and PPARδ ligands produce distinct biological effects.1999 J Biol Chem 274: 6718–6725). (L-783483 is 3-chloro-4-(3-(7-propyl-3-trifluoromethyl-6-benz-[4,5]-isoxazoloxy) propylthio)phenylacetic acid, Ex. 20 in WO97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/nL benzamide and 0.5 mM PMSF) containing 0.1% non-fat dry milk and 5.0 nM [$^3$H$_2$]L-797773, (34 Ci/mmole), ±test compound. (L-797733 is (3-(4-(3-phenyl-7-propyl-6-benz-[4,5]-isoxazoloxy)butyloxy))phenylacetic acid, Ex.62 in WO97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B) Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5X)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10$^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5X)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate±increasing concentrations of test compound. Since the compounds were solubilized in DMSO, control cells were incubated with equivalent. concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.). Partial agonism was determined by comparison of maximal transactivation activity with standard PPAR agonists such as rosiglitazone and pioglitazone. If the maximal stimulation of transactivation was less than 50% of the effect observed with standard compounds, then the compound was designated as a partial agonist.

C) In Vivo Studies

Male db/db mice (10–11 week old C57B1/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, and triglyceride concentrations were determined from blood obtained by tail bleeds at 3–5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

EXAMPLES

The following Examples are provided to illustrate the invention, including methods of making the compounds of the invention, and are not to be construed as limiting the invention in any manner. The scope of the invention is defined by the appended claims.

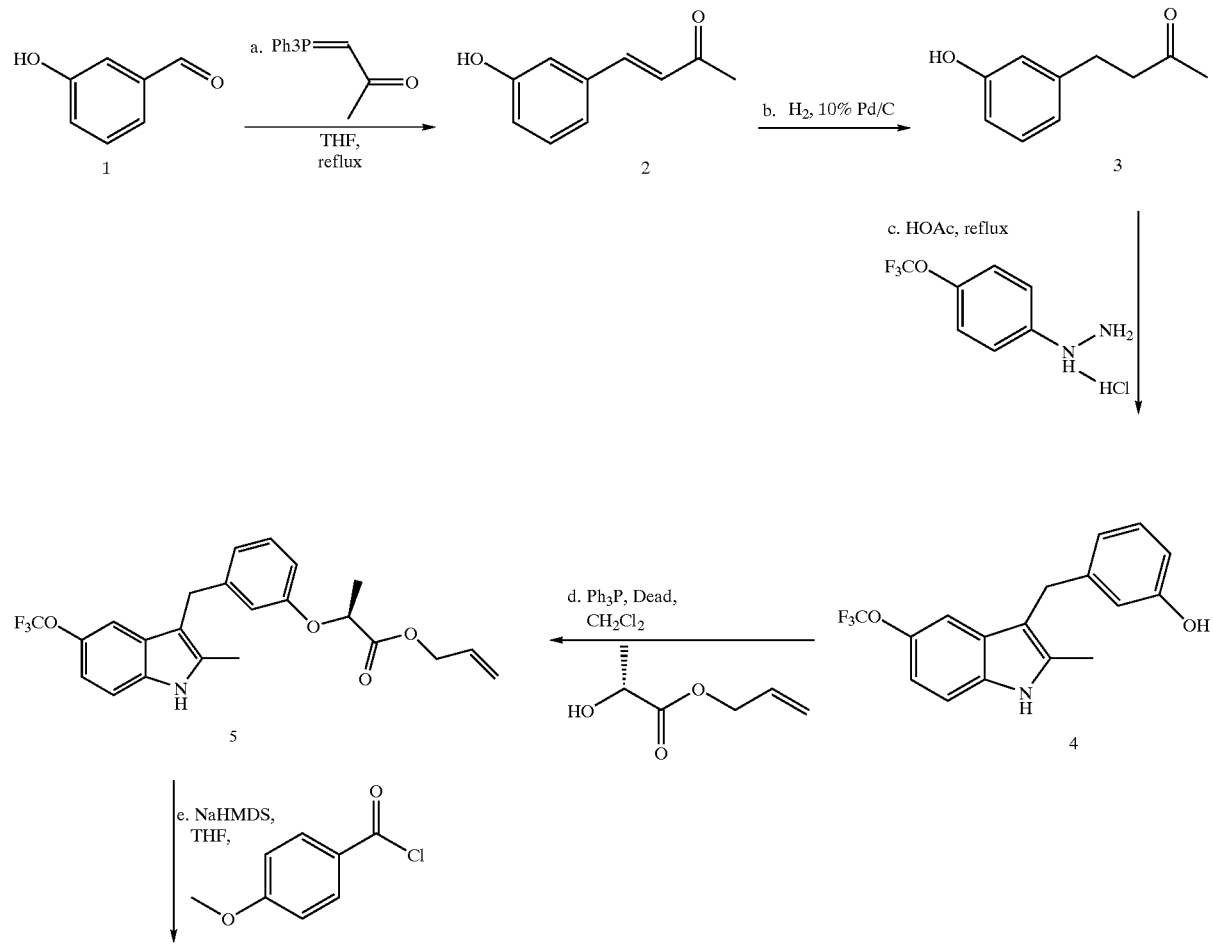

Scheme 1.
Synthesis of Example 1

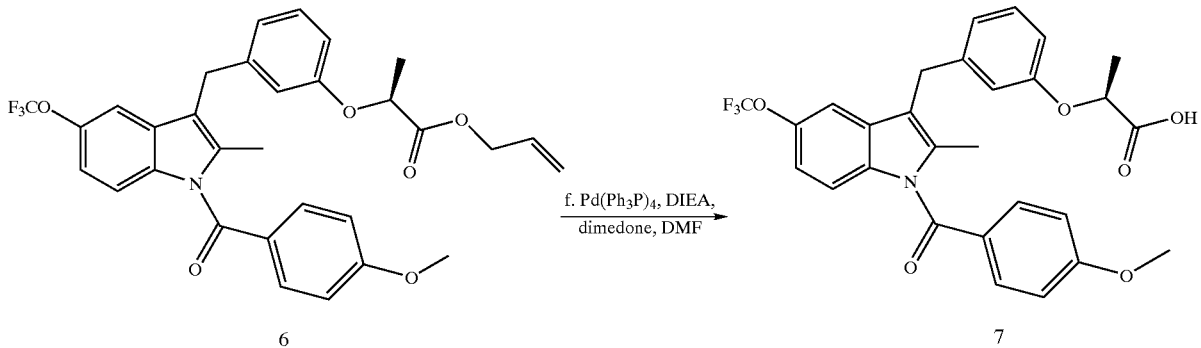

f. Pd(Ph$_3$P)$_4$, DIEA, dimedone, DMF

6 → 7

EXAMPLE 1

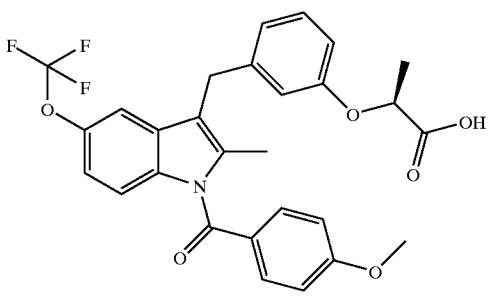

(2S)-2-(3-{[1-(4-Methoxybenzoyl)-2-methyl-5-(trifluoromethoxy)-1H-indol-3-yl]methyl}phenoxy)propanoic acid Step 1. (3E)-4-(3-Hydroxyphenyl)-3-buten-2-one (2)

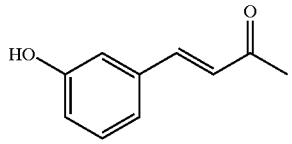

3-Hydroxybenzaldehyde (4.0 g, 32.8 mmole) was dissolved in THF (165 mL) and 1-triphenylphosphoranylidene-2-propanone (20.9 g, 65.6 mmole) was added. The solution was heated to reflux until TLC monitoring determined reaction was complete. Silica gel chromatography with 20% ethyl acetate in hexanes as eluent was used to isolate the title compound in 65% yield.

$^1$H NMR (400 MHz, CDCl$_3$): δ7.50 (d, 1H), 7.30 (t, 1H), 7.14 (d, 1H), 7.09 (s, 1H), 6.93 (dd, 1H), 6.72 (d, 1H), 5.70 (s, 1H), 2.42 (s, 3H).

Step 2. 4-(3-Hydroxyphenyl)-2-butanone (3):

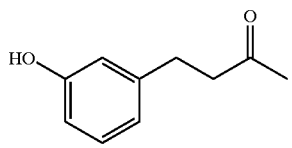

Compound 2 from Step 1 (2.0 g, 12.3 mmole) was dissolved in ethyl acetate (120 mL). The reaction vessel was evacuated and charged with nitrogen gas. Then 10% palladium on activated charcoal was added (200 mg). The reaction vessel was then evacuated and charged with hydrogen gas and the reaction monitored by TLC. After 1 hour the reaction was filtered over celite and the filtrate evaporated to give the title compound in nearly quantitative yield.

$^1$HNMR (400 MHz, CDCl3): δ7.17 (t, 1H), 6.78 (d, 1H), 6.70 (s, 1H), 6.69 (d, 1H), 5.00 (br s, 1H), 2.88 (t, 2H), 2.78 (t, 2H), 2.18 (s, 3H).

Step 3. 3-{[2-Methyl-5-(trifluoromethoxy)-1H-indol-3-yl]methyl}phenol (4)

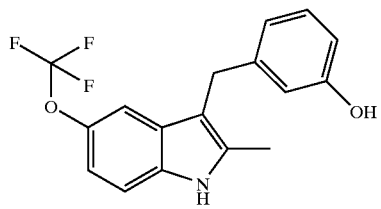

p-Trifluoromethoxyphenyl hydrazine hydrochloride (2.58 gr, 11.3 mmole) and Compound 3 (1.86 gl, 11.3 mmole) were stirred in acetic acid at 110° C. for 45 minutes, at which time reaction was complete by HPLC. Acetic acid was removed by rotary evaporation and the resulting residue was purified by normal phase chromatography to give an orange oil (2.83 gr, 78%).

$^1$H NMR (400 MHz, CDCl3): δ7.91 (br s, 1H), 7.1–7.25 (m, 3H), 6.99 (m, 1H), 6.83 (d, 1H), 6.62 (m, 2H), 5.05 (br s, 1H), 3.99 (s, 2H), 2.38 (s, 3H).

Step 4. Allyl (2S)-2-(3-{[2-methyl-5-(trifluoromethoxy)-1H-indol-3-yl]methyl}phenoxy)propanoate (5)

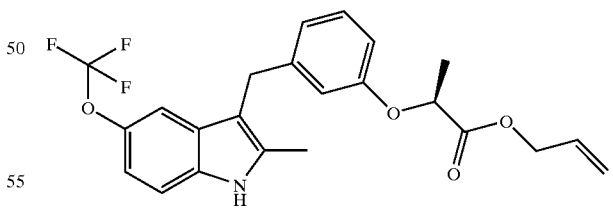

The phenolic indole (4) (50 mg, 0.16 mmole) was dissolved in dichloromethane (2 mL). To the phenol solution was added (S)-allyl lactate (24 mg, 0.19 mmole), triphenylphosphine (50 mg, 0.19 mmole), and diethylazodicarboxylate (DEAD) (0.030 mL, 0.19 mmole) and the reaction was monitored by TLC. Once complete the reaction was purified by silica gel chromatography to give the title compound (44.1 mg, 64%).

$^1$H NMR (400 MHz, CDCl$_3$): δ7.93 (s, 1H), 7.24 (d, 1H), 7.21 (s, 1H), 7.17 (t, 1H), 6.98 (d, 1H), 6.86 (d, 1H), 6.73 (s,

1H), 6.68 (d, 1H), 5.84 (m, 1H), 5.22 (m, 2H), 4.72 (q, 1H), 4.58 (m, 2H), 4.01 (s, 2H), 2.39 (s, 3H), 1.59 (d, 3H)

Step 5. Allyl (2S)-2-(3-{[1-(4-Methoxybenzoyl)-2-methyl-5-(trifluoromethoxy)-1H-indol-3-yl]methyl}phenoxy)propanoate (6)

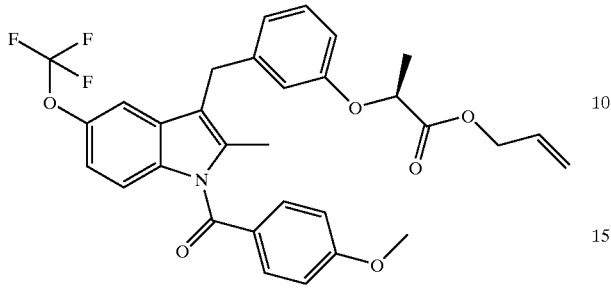

Compound 5 (467 mg, 1.1 mmole) was dissolved in tetrahydrofuran (11 mL) and cooled to −78° C. Sodium bis(trimethylsilyl)amide 1.3 mL of a 1.0N solution in THF) was added and the reaction mixture was stirred for 10 minutes. p-Anisoyl chloride (221 mg, 1.3 mmole) was then added. The reaction was warmed to 0° C. then quenched with saturated ammonium chloride and diluted with ether (100 ml). The ether layer was washed with water (2×), brine (1×) and dried over sodium sulfate followed by filtration and evaporation of the filtrate giving the title compound after silica gel chromatography (490 mg, 79%).

$^1$H NMR (400 MHz, CDCl$_3$): δ7.77 (d, 2H), 7.21 (t, 1H), 7.18 (s, 1H), 7.24 (d, 1H), 7.01 (d, 2H), 6.91 (d, 1H), 6.87 (d, 1H), 6.76 (s, 1H), 6.71 (d, 1H), 5.84 (m, 1H), 5.22 (m, 2H), 4.72 (q, 1H), 4.58 (m, 2H), 4.02 (s, 2H), 3.93 (s, 3H), 2.40 (s, 3H), 1.61 (d, 3H).

Step 6. (2S)-2-(3-{[1-(4-Methoxybenzoyl)-2-methyl-5-(trifluoromethoxy)-1H-indol-3-yl]methyl}phenoxy)propanoic acid (7)

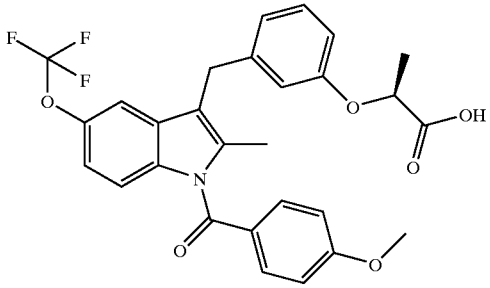

Compound 6 (490 mg, 0.86 mmole) was dissolved in DMF (9 mL). 5,5-Dimethyl-1,3-cyclohexanedione (181 mg, 1.29 mmole), N,N-diisopropylethylamine (0.225 mL, 1.29 mmole) and (tetrakistriphenylphoshine)palladium (50 mg, 0.043 mmole) were then added and the solution stirred for 2 hours. Then aqueous ammonium chloride was added and the solution was extracted repeatedly with dichloromethane. The combined organics were dried over sodium sulfate, filtered and the filtrate was evaporated. The crude isolate was then purified by silica gel chromatography to give the title compound (395 mg, 87%).

$^1$H NMR (400 MHz, CDCl$_3$): 7.76 (d, 2H), 7.23 (t, 1H), 7.18 (s,1H), 7.02 (d, 1H), 7.01 (d, 2H), 6.92 (d, 1H), 6.91 (d, 1H), 6.76 (s, 1H), 6.75 (d, 1H), 4.76 (q, 1H), 4.04 (s, 2H), 3.94 (s, 3H), 2.41 (s, 3H), 1.63 (d, 3H).

EXAMPLES 2–31

The following compounds were prepared in a similar fashion to that shown in the above scheme and in Example 1 from commercially available starting materials.

EXAMPLE 2

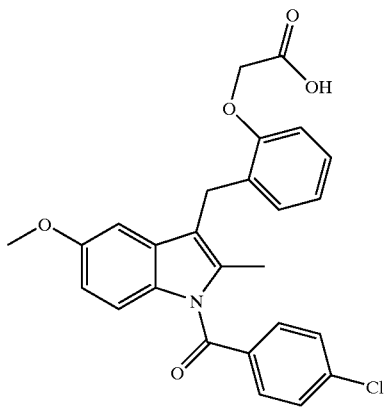

2-(2-{[1-(4-Chlorobenzoyl)-2-methyl-5-(methoxy)-1H-indol-3-yl]methyl}phenoxy)acetic acid $^1$H NMR (400 MHz, CDCl$_3$): δ7.69(d,2H), 7.49(d,2H), 7.21 (dt,1H), 7.05 (dd,1H), 6.93 (m,2H), 6.83 (m,2H), 6.66 (dd,1H), 4.78 (s, 2H), 4.10 (s, 2H), 3.74 (s, 3H), 2.38 (s, 3H).

EXAMPLE 3

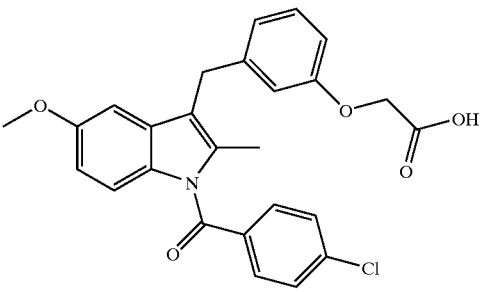

2-(3-{[1-(4-Chlorobenzoyl)-2-Methyl-5-(methoxy)-1H-indol-3-yl]methyl}phenoxy)acetic acid $^1$H NMR (400 MHz, CDCl$_3$): δ7.69(d, 2H), 7.49(d, 2H), 7.24 (t, 1H), 6.94 (d, 1H), 6.88 (d, 1H), 6.80 (d, 2H), 6.76 (dd, 1H), 6.66 (dd, 1H), 4.64 (s, 2H), 4.03 (s, 2H), 3.77 (s, 3H), 2.39 (s, 3H).

EXAMPLE 4

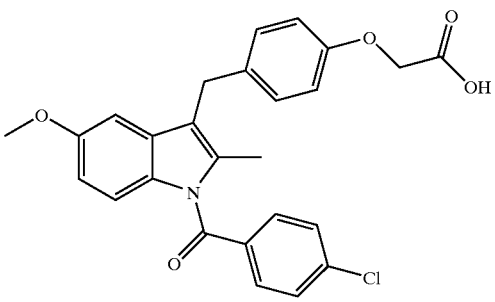

2-(4-{[1-(4-Chlorobenzoyl)-2-methyl-5-(methoxy)-1H-indol-3-yl]methyl}phenoxy)acetic acid $^1$H NMR (400 MHz, CDCl$_3$): δ7.68(d, 2H), 7.49(d, 2H), 7.16 (m, 2H), 6.85 (m, 3H) 6.79 (d, 1H), 6.66 (dd, 1H), 4.64 (s, 2H), 3.99 (s, 2H), 3.76 (s, 3H), 2.39 (s, 3H).

EXAMPLE 5

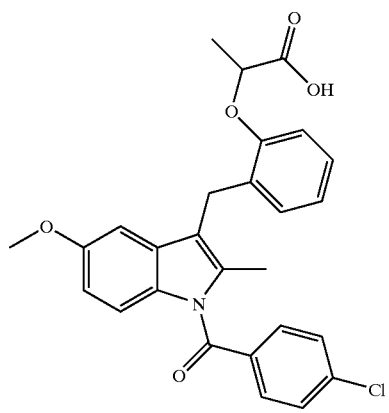

2-(2-{[1-(4-Chlorobenzoyl)-2-methyl-5-(methoxy)-1H-indol-3-yl]methyl}phenoxy)propanoic acid $^1$H NMR (400 MHz, CDCl$_3$): δ7.69(d, 2H), 7.48(d, 2H), 7.18(m, 1H), 7.05 (d, 1H), 6.91 (m, 2H), 6.82 (m, 2H), 6.65 (dd, 1H), 4.92 (q, 1H), 4.09 (q, 2H), 3.74 (s, 3H), 2.37 (s, 3H) 1.71 (d, 3H).

EXAMPLE 6

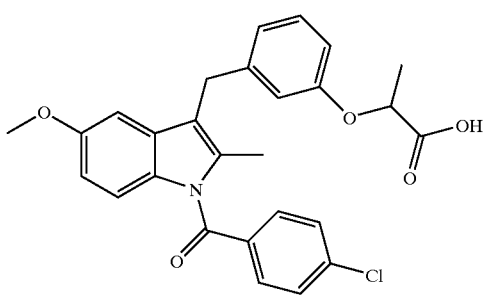

2-(3-{[1-(4-Chlorobenzoyl)-2-methyl-5-(methoxy)-1H-indol-3-yl]methyl}phenoxy)propanoic acid $^1$H NMR (400 MHz, CDCl$_3$): δ7.69(d, 2H), 7.49(d, 2H), 7.21(t, 1H), 6.90 (d, 1H), 6.88 (d, 1H), 6.81 (d, 1H), 6.78 (br t, 1H), 6.73 (dd, 1H), 6.65 (dd, 1H), 4.75 (q. 1H), 4.01 (s, 2H), 3.77 (s, 3H), 2.38 (s, 3H) 1.64 (d, 3H).

EXAMPLE 7

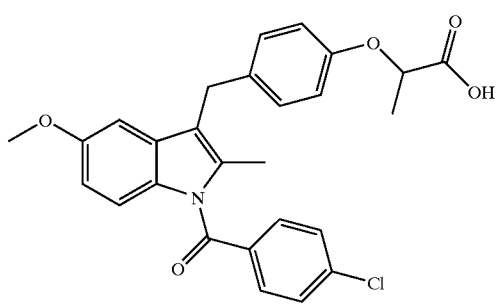

2-(4-{[1-(4-Chlorobenzoyl)-2-methyl-5-(methoxy)-1H-indol-3-yl]methyl}phenoxy)propanoic acid $^1$H NMR (300 MHz, CDCl$_3$): δ7.66 (d, 2H), 7.48 (d, 2H), 7.17 (m, 2H), 6.80 (m, 4H), 6.62 (d, 1H), 4.74 (q, 1H), 3.96 (s, 2H), 3.75 (s, 3H), 2.38 (s, 3H), 1.61 (d, 3H); ES_MS (M+1) 478, 480.

EXAMPLE 8

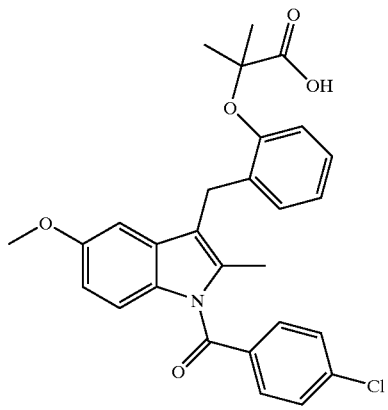

2-(2-{[1-(4-Chlorobenzoyl)-2-methyl-5-(methoxy) 1H-indol-3-yl]methyl}phenoxy)-2-methylpropanoic acid $^1$H NMR (400 MHz, CDCl$_3$): δ7.69(d, 2H), 7.49(d, 2H), 7.13(m,1H), 7.01 (d,1H), 6.89 (m,3H), 6.77 (d, 1H), 6.66 (dd, 1H), 4.04 (s, 2H), 3.73(s, 3H), 2.36 (s, 3H) 1.69(s, 6H).

EXAMPLE 9

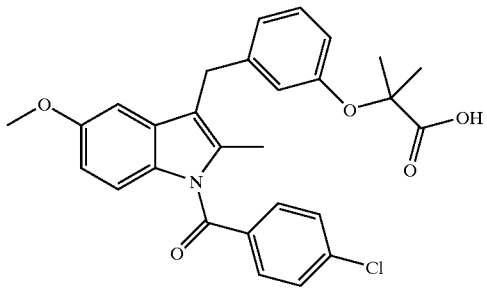

2-(3-{[1-(4-Chlorobenzoyl)-2-methyl-5-(methoxy)-1H-indol-3-yl]methyl}phenoxy)-2-methylpropanoic acid $^1$H NMR (400 MHz, CDCl$_3$): δ7.69(d, 2H), 7.49(d, 2H), 7.19(m, 2H), 6.96 (d, 1H), 6.88 (d, 1H), 6.79 (m, 2H), 6.66 (dd, 1H), 4.00 (s, 2H), 3.76 (s, 3H), 2.38 (s, 3H) 1.55 (s, 6H).

EXAMPLE 10

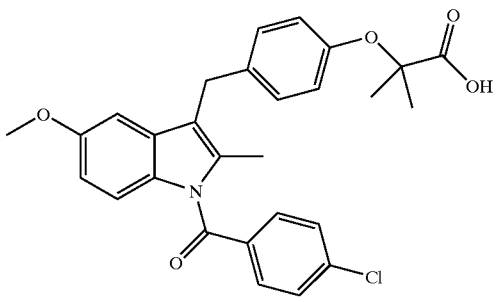

2-(4-{[1-(4-Chlorobenzoyl)-2-methyl-5-(methoxy)-1H-indol-3-yl]methyl}phenoxy)-2-methylpropanoic acid $^1$H NMR (400 MHz, CDCl$_3$): δ7.69(d, 2H), 7.49(d, 2H), 7.24(d, 2H), 6.88 (m, 3H), 6.79 (d, 1H), 6.66 (d, 1H), 4.00 (s, 2H), 3.76 (s, 3H), 2.39 (s, 3H) 1.57 (s, 6H).

EXAMPLE 11

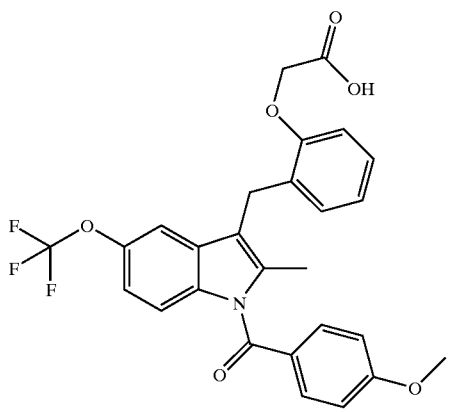

2-(2-{[1-(4-Methoxybenzoyl)-2-methyl-5-(trifluoromethoxy)-1H-indol-3-yl]methyl}phenoxy) acetic acid $^1$H NMR (400 MHz, CDCl$_3$): δ7.74 (d, 2H), 7.28 (s, 1H), 7.21 (dt, 1H), 7.05 (m, 2H), 7.01 (d, 2H), 6.92 (t, 1H), 6.89 (dd, 1H), 6.82 (d, 1H), 4.78 (s, 2H), 4.13 (s, 2H), 3.93 (s, 3H), 2.41 (s, 3H).

EXAMPLE 12

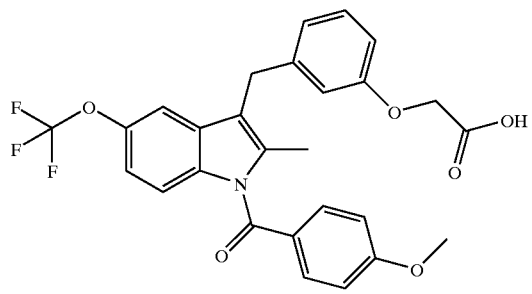

2-(3-{[1-(4-Methoxybenzoyl)-2-Methyl-5-(trifluoromethoxy)-1H-indol-3-yl]methyl}phenoxy) acetic acid $^1$H NMR (400 MHz, CDCl$_3$): δ7.78 (d, 2H), 7.22 (t, 1H), 7.18 (s, 1H), 7.01 (m, 3H), 6.92 (m, 2H), 6.80 (s, 1H), 6.78 (d, 1H), 4.63 (s, 2H), 4.15 (s, 2H), 3.93 (s, 3H), 2.42 (s, 3H).

EXAMPLE 13

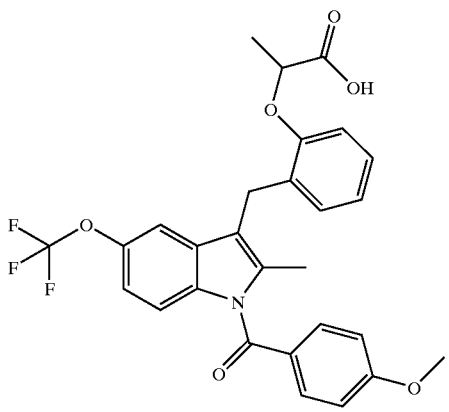

2-(2-{[1-(4-methoxybenzoyl)-2-Methyl-5-(trifluoromethoxy)-1H-indol-3-yl]methyl}phenoxy) propanoic acid $^1$H NMR (400 MHz, CDCl$_3$): δ7.74 (d, 2H), 7.25 (s, 1H), 7.19 (dt, 1H), 7.05 (d, 1H) 7.03 (d, 1H), 7.00 (d, 2H), 6.90 (m, 2H), 6.82 (d, 1H), 4.93 (q, 1H), 4.12 (q, 2H), 3.93 (s, 3H), 2.41 (s, 3H), 1.72 (d, 3H).

EXAMPLE 14

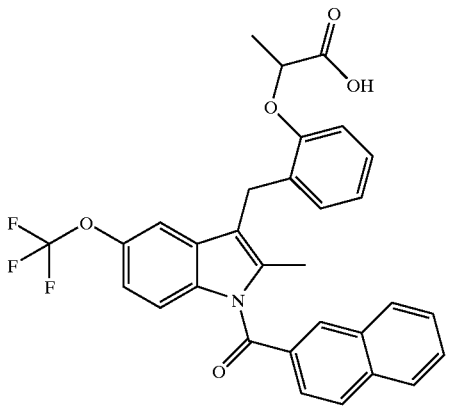

2-(2-{[1-(2-naphthoyl)-2-Methyl-5-(trifluoromethoxy)-1H-indol-3-yl]methyl}phenoxy) propanoic acid $^1$H NMR (500 MHz, DMSO-d$_6$): δ12.96 (s, 1H), 8.35 (s, 1H), 8.07 (m, 3H), 7.76 (dd, 1H), 7.70 (t, 1H), 7.63 (t, 1H), 7.46 (s, 1H), 7.13 (m, 2H), 7.09 (d, 1H), 6.99 (s, 1H), 6.85 (t, 2H), 4.91 (q, 1H), 4.06 (s, 2H), 2.31 (s, 3H), 1.51 (d, 3H).

EXAMPLE 15

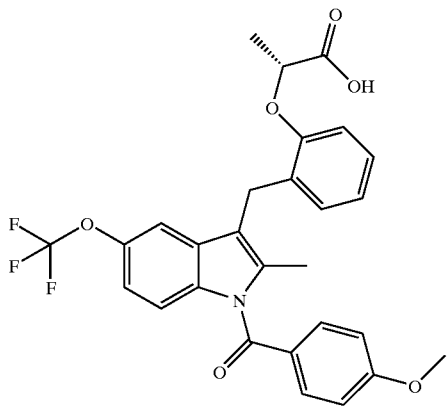

(2R)-2-(2-{[1-(4-methoxybenzoyl)-2-Methyl-5-(trifluoromethoxy)-1H-indol-3-yl]methyl}phenoxy) propanoic acid $^1$H NMR (500 MHz, CDCl$_3$): δ7.74 (d, 2H), 7.25 (s, 1H), 7.19 (dt, 1H), 7.05 (d, 1H), 7.03 (d, 1H), 7.00 (d, 2H), 6.90 (m, 2H), 6.82 (d, 1H), 4.93 (q, 1H), 4.12 (q, 2H), 3.93 (s, 3H), 2.41(s, 3H), 1.72 (d, 3H).

EXAMPLE 16

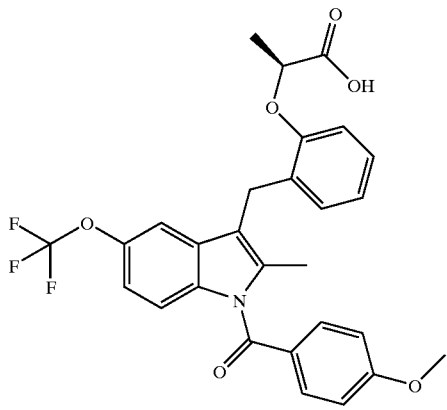

(2S)-2-(2-{[1-(4-Methoxybenzoyl)-2-methyl-5-(trifluoromethoxy)-1H-indol-3-yl]methyl}phenoxy) propanoic acid $^1$H NMR (500 MHz, CDCl$_3$): δ7.74 (d, 2H), 7.25 (s, 1H), 7.19 (dt, 1H), 7.05 (d, 1H) 7.03 (d, 1H), 7.00 (d, 2H), 6.90 (m, 2H), 6.82 (d, 1H), 4.93 (q, 1H), 4.12 (q, 2H), 3.93 (s, 3H), 2.41 (s, 3H), 1.72 (d, 3H).

EXAMPLE 17

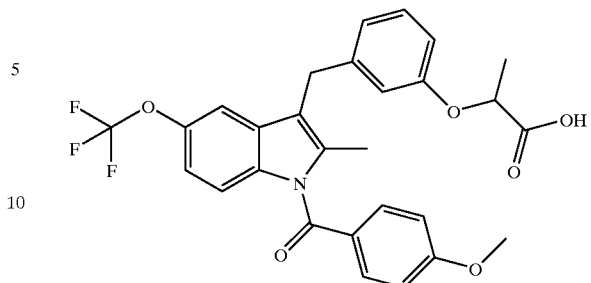

2-(3-{[1-(4-Methoxybenzoyl)-2-methyl-5-(trifluoromethoxy)-1H-indol-3-yl]methyl}phenoxy) propanoic acid $^1$HNMR (400 MHz, CDCl$_3$): 7.76 (d, 2H), 7.23 (t, 1H), 7.18 (s,1H), 7.02 (d, 1H), 7.01 (d, 2H), 6.92 (d, 1H), 6.91 (d, 1H), 6.76 (s, 1H), 6.75 (d, 1H), 4.76 (q, 1H), 4.05 (s, 2H), 3.94 (s, 3H), 2.41 (s, 3H), 1.63 (d, 3H).

EXAMPLE 18

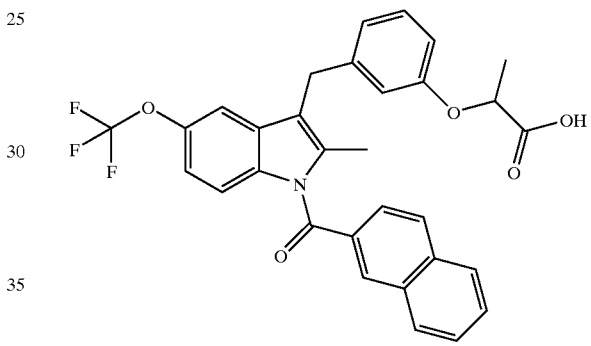

2-(3-{[1-(2-Naphthoyl)-2-methyl-5-(trifluoromethoxy)-1H-indol-3-yl]methyl }phenoxy) propanoic acid $^1$HNMR (400 MHz, CDCl$_3$): d 8.30 (s, 1H), 7.97 (m, 3H), 7.80 (d, 1H), 7.68 (t, 1H), 7.61 (t, 1H), 7.24 (t, 1H), 7.20 (s, 1H), 7.03 (d, 1H), 6.92 (d, 1H), 6.86 (d, 1H), 6.80 (s, 1H), 6.75 (d, 1H), 4.78 (q, 1H), 4.06 (s, 2H), 2.41 (s, 3H), 1.65 (d, 3H)

EXAMPLE 19

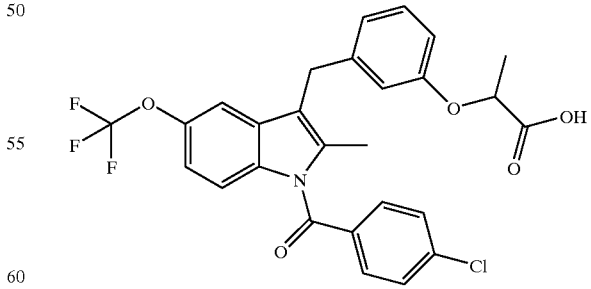

2-(3-{[1-(4-Chlorobenzoyl)-2-methyl-5-(trifluoromethoxy)-1H-indol-3-yl]methyl}phenoxy) propanoic acid $^1$H NMR (400 MHz, CDCl$_3$): δ6.69 (d, 2H), 7.50 (d, 2H), 7.24 (s, 1H), 7.15 (t, 1H), 7.03 (m, 2H), 6.90 (m, 2H), 6.79

(d, 1H), 4.91 (q, 1H), 4.07 (dd, 2H), 2.38 (s, 3H), 1.72 (d, 3H); ES–MS (M+1) 532, 534

EXAMPLE 20

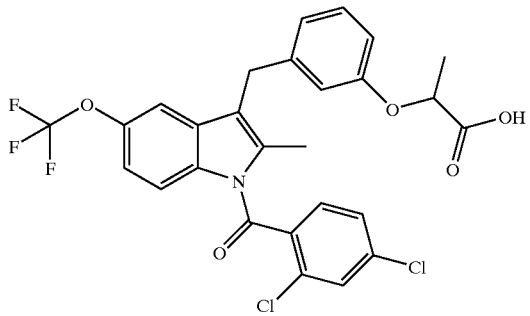

2-(3-{[1-(2,4-Dichlorobenzoyl)-2-methyl-5-(trifluoromethoxy)-1H-indol-3-yl]methyl}phenoxy) propanoic acid ¹H NMR (400 MHz, CDCl₃): δ7.49 (m, 4H), 7.24 (s, 1H), 7.18 (t, 1H), 6.99 (m, 2H), 6.87 (t, 1H), 6.78 (d, 1H), 4.93 (q, 1H), 4.08 (dd, 2H), 2.21 (s, 3H), 1.71 (d, 3H); ES–MS (M+1) 566, 568, 570.

EXAMPLE 21

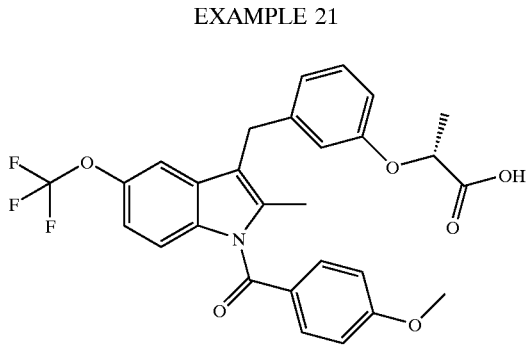

(2R)-2-(3-{[1-(4-Methoxybenzoyl)-2-methyl-5-(trifluoromethoxy)-1H-indol-3-yl]methyl}phenoxy) propanoic acid ¹H NMR (400 MHz, CDCl₃): 7.76 (d, 2H), 7.23 (t, 1H), 7.18 (s, 1H), 7.02 (d, 1H), 7.01 (d, 2H), 6.92 (d, 1H), 6.91 (d, 1H), 6.76 (s, 1H), 6.75 (d, 1H), 4.76 (q, 1H), 4.05 (s, 2H), 3.94 (s, 3H), 2.41 (s, 3H), 1.63 (d, 3H).

EXAMPLE 22

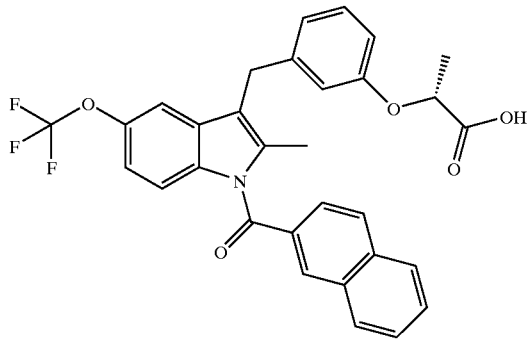

(2R)-2-(3-{[1-(2-Naphthoyl)-2-methyl-5-(trifluoromethoxy)-1H-indol-3-yl]methyl}phenoxy) propanoic acid ¹H NMR (400 MHz, CDCl₃): d 8.30 (s, 1H), 7.97 (m, 3H), 7.80 (d, 1H), 7.68 (t, 1H), 7.61 (t, 1H), 7.24 (t, 1H), 7.20 (s, 1H), 7.03 (d, 1H), 6.92 (d, 1H), 6.86 (d, 1H), 6.80 (s, 1H), 6.75 (d, 1H), 4.78 (q, 1H), 4.06 (s, 2H), 2.41 (s, 3H), 1.65 (d, 3H)

EXAMPLE 23

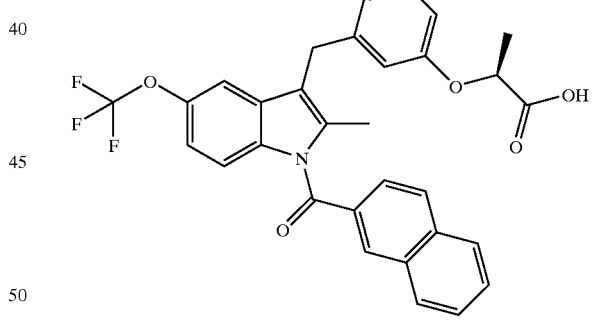

(2S)-2-(3-{[1-(2-Naphthoyl)-2-methyl-5-(trifluoromethoxy)-1H-indol-3-yl]methyl}phenoxy) propanoic acid ¹H NMR (400 MHz, CDCl₃): d 8.30 (s, 1H), 7.97 (m, 3H), 7.80 (d, 1H), 7.68 (t, 1H), 7.61 (t, 1H), 7.24 (t, 1H), 7.20 (s, 1H), 7.03 (d, 1H), 6.92 (d, 1H), 6.86 (d, 1H), 6.80 (s, 1H), 6.75 (d, 1H), 4.78 (q, 1H), 4.06 (s, 2H), 2.41 (s, 3H), 1.65 (d, 3H)

EXAMPLE 24

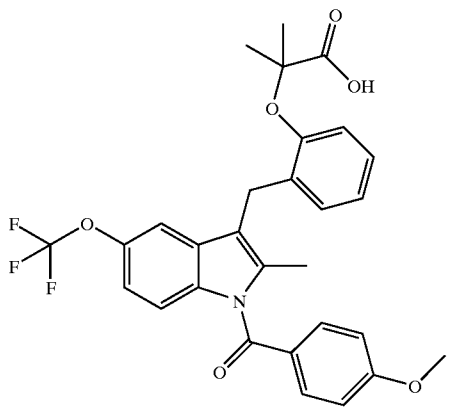

2-(2-{[1-(4-Methoxybenzoyl)-2-methyl-5-(trifluoromethoxy)-1H-indol-3-yl]methyl}phenoxy)-2-methylpropanoic acid $^1$H NMR (400 MHz, CDCl$_3$): δ7.74 (d, 2H), 7.15 (m, 2H), 7.01 (m, 4H), 6.85 (m, 3H), 4.08 (s, 2H), 3.93 (s, 3H), 2.39 (s, 3H), 1.68 (s, 6H); ES–MS (M+1) 542.

EXAMPLE 25

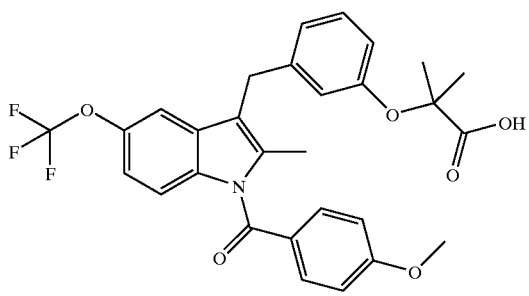

2-(3-{[1-(4-Methoxybenzoyl)-2-methyl-5-(trifluoromethoxy)-1H-indol-3-yl]methyl}phenoxy)-2-methylpropanoic acid $^1$H NMR (400 MHz, CDCl$_3$): δ7.76 (d, 2H), 7.19 (m, 2H), 7.00 (m, 4H), 6.82 (d, 2H), 6.78 (m, 2H), 4.22 (s, 2H), 3.91 (s, 3H), 2.21 (s, 3H), 1.57 (s, 6H); ES–MS (M+1) 542.

EXAMPLE 26

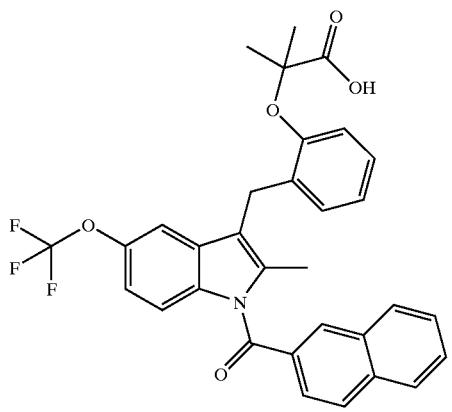

2-(2-{[1-(2-Naphthoyl)-2-methyl-5-(trifluoromethoxy)-1H-indol-3-yl]methyl}phenoxy)-2-methylpropanoic acid $^1$H NMR (400 MHz, CDCl$_3$): δ8.29 (s, 1H), 9.98 (m, 3H), 7.79 (d, 1H), 6.15 (m, 2H), 7.20 (s, 1H), 7.17 (t, 1H), 7.05 (m, 2H), 6.91 (t, 1H), 6.84 (m, 2H), 4.09 (s, 2H), 2.39 (s, 3H), 1.70 (s, 6H); ES–MS (M+1) 562.

EXAMPLE 27

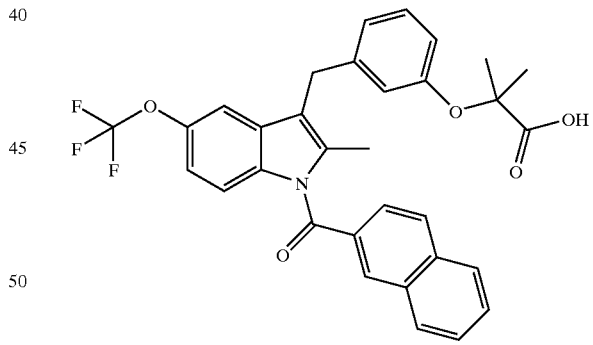

2-(3-{[1-(2-Naphthoyl)-2-methyl-5-(trifluoromethoxy)-1H-indol-3-yl]methyl}phenoxy)-2-methylpropanoic acid $^1$H NMR (400 MHz, CDCl$_3$): δ8.31 (s, 1H), 7.95 (m, 3H), 7.80 (d, 1H), 7.65 (m, 2H), 7.20 (m, 2H), 7.03 (d, 1H), 6.97 (d, 1H), 6.83 (d, 1H), 6.79 (M, 2H), 4.07 (s, 2H), 2.21 (s, 3H), 1.58 (s, 6H); ES–MS (M+1) 363.

EXAMPLE 28

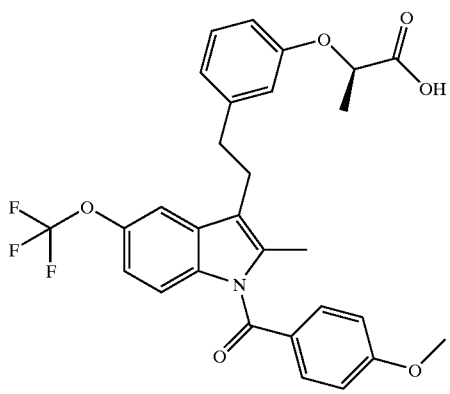

(2R)-2-(3-{2-[1-(4-Methoxybenzoyl)-2-methyl-5-(trifluoromethoxy)-1H-indol-3yl]ethyl}phenoxy)propionic acid $^1$H NMR (400 MHz, CDCl$_3$): δ7.75–7.60 (br m, 2H), 7.33-7.29 (m, 2H), 7.21 (t, 1H), 7.02 (d, 1H), 6.97–6.95 (m, 2H), 6.88 (d, 1H), 6.80 (d, 1H), 6.01 (s, 1H), 4.51 (br m, 1H), 3.92 (s, 3H), 3.11–3.02 (m, 2H), 2.81–2.75 (m, 2H), 1.65 (s, 3H), 1.56 (d, 3H); ES–MS (M+1) 542.

EXAMPLE 29

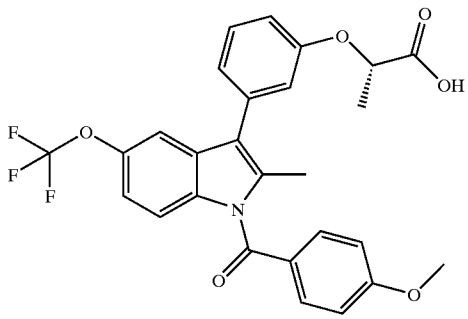

(2S)-2-{3-[1-(4-methoxybenzoyl)-2-methyl-5-(trifluoromethoxy)-1H -indol-3-yl]phenoxy}propionic acid $^1$H NMR (500 MHz, CDCl$_3$): δ7.81 (d, 2H), 7.46 (t, 1H), 7.39 (br s, 1H), 7.16 (d, 1H), 7.11 (d, 1H), 7.04 (m, 3H), 6.97 (m, 2H), 4.91 (q, 1H), 3.95 (s, 3H), 2.44 (s, 3H), 1.74 (d, 3H).

EXAMPLE 30

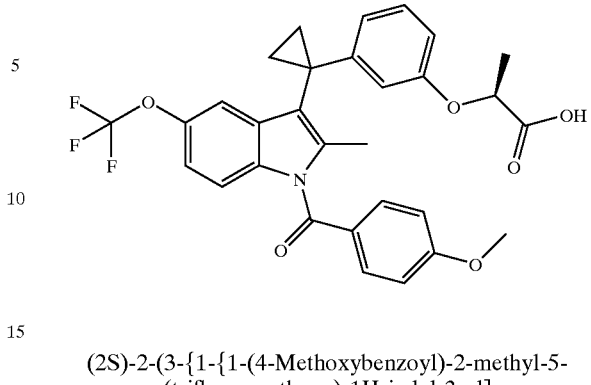

(2S)-2-(3-{1-{1-(4-Methoxybenzoyl)-2-methyl-5-(trifluoromethoxy)-1H-indol-3-yl]cyclopropyl}phenoxy)propanoic acid $^1$H NMR (500 MHz, CDCl$_3$): δ7.77 (d, 2H), 7.46, (s, 1H), 7.18 (t, 1H), 7.02 (m, 3H), 6.92 (d, 1H), 6.75 (d, 2H), 6.69–6.66 (m, 2H), 4.70 (q, 1H), 3.94 (s, 3H), 2.47 (s, 3H), 1.63 (d, 3H), 1.50 (m, 2H), 1.33 (m, 2H); ES–MS (M+1) 554.

EXAMPLE 31

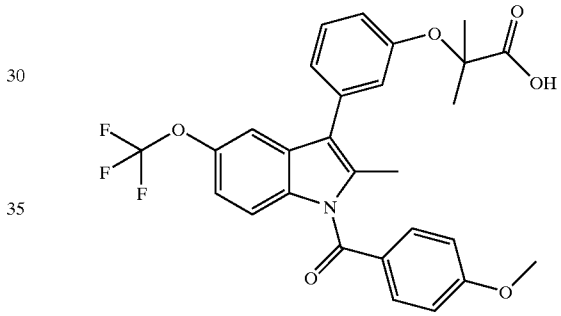

2-{3-[1-(4-Methoxybenzoyl)-2-methyl-5-(trifluoromethoxy)-1H-indol-3-yl]phenoxy}-2-methylpropanoic acid $^1$H NMR (500 MHz, CDCl$_3$): δ7.80 (d, 2H), 7.43 (t, 1H), 7.38 (br s, 1H), 7.20 (d, 1H), 7.10 (d, 1H), 7.02(m, 5H), 3.94 (s, 3H), 2.43 (s, 3H), 1.69 (s, 6H).

What is claimed is:

1. A compound of formula I:

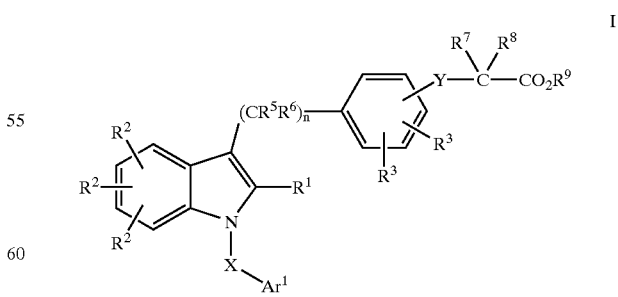

wherein:

$R^1$ is methyl, optionally substituted with 1–3 F;

$R^2$, $R^3$ and $R^4$ are each independently selected from the group consisting of H, halogen, $C_1$–$C_6$ alkyl, $C_2$–$C_6$ alkenyl, $C_2$–$C_6$ alkynyl, $C_3$–$C_8$ cycloalkyl, aryl, $OC_1$–$C_6$ alkyl, $OC_2$–$C_6$ alkenyl, $OC_2$–$C_6$ alkynyl, O-aryl, OH, $SC_1$–$C_6$ alkyl, $SC_2$–$C_6$ alkenyl, $SC_2$–$C_6$ alkynyl, $SO_2C_1$–$C_6$ alkyl, $SO_2C_2$–$C_6$ alkenyl, $SO_2C_2$–$C_6$ alkynyl, $OCON(R_5)_2$, $OCO(C_1$–$C_6$-alkyl) and CN, wherein all instances of alkyl, alkenyl and alkynyl are optionally linear or branched and all instances of alkyl, alkenyl, alkynyl, cycloalkyl and aryl are optionally substituted with 1–5 substituents independently selected from the group consisting of halogen, aryl, O-aryl and OMe;

$R^5$ and $R^6$ are, at each occurrence, independently selected from the group consisting of H, F, OH and $C_1$–$C_5$ alkyl, and $R^5$ and $R^6$ groups that are on the same carbon atom optionally may be joined to form a $C_3$–$C_6$ cycloalkyl group;

$R^7$ and $R^8$ are each independently selected from the group consisting of H, F, and $C_{1-5}$ alkyl, or $R^7$ and $R^8$ optionally may be joined to form a $C_3$–$C_6$ cycloalkyl group;

$R^9$ is selected from the group consisting of H and $C_1$–$C_5$ alkyl, said alkyl being optionally linear or branched;

$Ar^1$ is phenyl, 1-naphthyl, 2-naphthyl, pyridyl or quinolyl wherein $Ar^1$ is substituted with 1–3 groups independently selected from $R^4$;

X is selected from the group consisting of C=O, $S(O)_2$, $CH_2$, $CH(CH_3)$, $C(CH_3)_2$, $CF_2$, and cyclopropylidene;

Y is O or S; and n is 0–5;

and pharmaceutically acceptable salts thereof.

2. The compound of claim 1 wherein:

$R^1$ is $CH_3$;

$R^2$, $R^3$ and $R^4$ are each independently selected from the group consisting of H, halogen, $C_1$–$C_6$ alkyl, $C_2$–$C_6$ alkenyl, $C_2$–$C_6$ alkynyl, $C_3$–$C_8$ cycloalkyl, aryl, $OC_1$–$C_6$ alkyl, $OC_2$–$C_6$ alkenyl, $OC_2$–$C_6$ alkynyl, O-aryl, OH, $SC_1$–$C_6$ alkyl, $SC_2$–$C_6$ alkenyl, $SC_2$–$C_6$ alkynyl, $OCON(R_5)_2$, $OCO(C_1$–$C_6$-alkyl) and CN, wherein all instances of alkyl, alkenyl and alkynyl are optionally linear or branched and all instances of alkyl, alkenyl, alkynyl, cycloalkyl and aryl are optionally substituted with 1–5 substituents independently selected from the group consisting of halogen, aryl, O-aryl and OMe; and X is selected from the group consisting of C=O, $CH_2$, $CH(CH_3)$, $C(CH_3)_2$, $CF_2$, and cyclopropylidene.

3. The compound of claim 1 wherein $R^2$, $R^3$, and $R^4$ are each independently selected from the group consisting of H, $OCH_3$, $OCF_3$, F, Cl and $CH_3$, wherein $CH_3$ is optionally substituted with 1–3 groups independently selected from F, Cl, and $OCH_3$.

4. The compound of claim 1 wherein $R^2$, $R^3$, and $R^4$ are each independently selected from the group consisting of H, $OCH_3$, $OCF_3$, and Cl.

5. The compound of claim 1 wherein $R^5$ and $R^6$ are H.

6. The compound of claim 1 wherein $R^7$ and $R^8$ are each independently $CH_3$ or H.

7. The compound of claim 1 wherein $R^9$ is H.

8. The compound of claim 1 wherein X is C=O.

9. The compound of claim 1 wherein Y is O.

10. The compound of claim 1 wherein n is 0, 1 or 2.

11. The compound of claim 1 wherein n is 1.

12. The compound of claim 1 wherein $Ar^1$ is phenyl, 1-naphthyl or 2-naphthyl.

13. The compound of claim 1 wherein $Ar^1$ is phenyl or 2-naphthyl, $Ar^1$ being substituted with 1–3 groups independently selected from $R^4$.

14. The compound of claim 1 wherein aryl is phenyl.

15. The compound of claim 1 wherein:

$R^1$ is $CH_3$;

$R^2$ is selected from the group consisting of H, $OCH_3$, and $OCF_3$;

$R^3$, $R^5$, $R^6$, and $R^9$ are H;

$R^4$ is selected from the group consisting of H, Cl, and $OCH_3$;

$R^7$ and $R^8$ are each independently selected from the group consisting of H and $CH_3$;

X is C=O;

Y is O;

and n is 1.

16. A compound which is selected from the group consisting of:

2S)-2-(3-{[1-(4-Methoxybenzoyl)-2-methyl-5-(trifluoromethoxy)-1H-indol-3-yl]methyl}phenoxy)propanoic acid;

2-(2-{[1-(4-Chlorobenzoyl)-2-methyl-5-(methoxy)-1H-indol-3-yl]methyl}phenoxy)acetic acid;

2-(3-{[1-(4-Chlorobenzoyl)-2Methyl-5-(methoxy)-1H-indol-3-yl]methyl}phenoxy)acetic acid;

2(4-{[1-(4-Chlorobenzoyl)-2-methyl-5-(methoxy)-1H-indol-3-yl]methyl}phenoxy)acetic acid;

2-(2-{[1-(4-Chlorobenzoyl)-2-methyl-5-(methoxy)-1H-indol-3-yl]methyl}phenoxy)propanoic acid;

2-(3-{[1-(4-Chlorobenzoyl)-2-methyl-5-(methoxy)-1H-indol-3-yl]methyl}phenoxy)propanoic acid;

2-(4-{[1-(4-Chlorobenzoyl)-2-methyl-5-(methoxy)-1H-indol-3-yl]methyl}phenoxy)propanoic acid;

2-(2-{[1-(4-Chlorobenzoyl)-2-methyl-5-(methoxy)-1H-indol-3-yl]methyl}phenoxy)-2-methylpropanoic acid;

2-(3-{[1-(4-Chlorobenzoyl)-2-methyl-5-(methoxy)-1H-indol-3-yl]methyl}phenoxy)-2-methylpropanoic acid;

2-(3-{[1-(4-Chlorobenzoyl)-2-methyl-5-(methoxy)-1H-indol-3-yl]methyl}phenoxy)-2-methylpropanoic acid;

2-(2-{[1-(4-Methoxybenzoyl)-2-methyl-5-(trifluoromethoxy)-1H-indol-3-yl]methyl}phenoxy)acetic acid;

2-(3-{[1-(4-Methoxybenzoyl)-2-Methyl-5-(trifluoromethoxy)-1H-indol-3-yl]methyl}phenoxy)acetic acid;

2-(2-{[1-(4-methoxybenzoyl)-2-Methyl-5-(trifluoromethoxy)-1H-indol-3-yl]methyl}phenoxy)propanoic acid;

2-(2-{[1-(2-naphthoyl)-2-Methyl-5-(trifluoromethoxy)-1H-indol-3-yl]methyl}phenoxy)propanoic acid;

(2R)-2-(2-{[1-(4-methoxybenzoyl)-2-Methyl-5-(trifluoromethoxy)-1H-indol-3-yl]methyl}phenoxy)propanoic acid;

(2S)-2-(2-{[1-(4-Methoxybenzoyl)-2-methyl-5-(trifluoromethoxy)-1H-indol-3-yl]methyl}phenoxy)propanoic acid;

2-(3-{[1-(4-Methoxybenzoyl)-2-methyl-5-(trifluoromethoxy)-1H-indol-3-yl]methyl}phenoxy)propanoic acid;

2-(3-{[1-(2-Naphthoyl)-2-methyl-5-(trifluoromethoxy)-1H-indol-3-yl]methyl}phenoxy)propanoic acid;

2-(3-{[1-(4-Chlorobenzoyl)-2-methyl-5-(trifluoromethoxy)-1H-indol-3-yl]methyl}phenoxy)propanoic acid;

2-(3-{[1-(2,4-Dichlorobenzoyl)-2-methyl-5-(trifluoromethoxy)-1H-indol-3-yl]methyl}phenoxy)propanoic acid;

(2R)-2-(3-{[1-(4-Methoxybenzoyl)-2-methyl-5-(trifluoromethoxy)-1H-indol-3-yl]methyl}phenoxy)propanoic acid;

(2R)-2-(3-{[1-(2-Naphthoyl)-2-methyl-5-(trifluoromethoxy)-1H-indol-3-yl]methyl}phenoxy)propanoic acid;

(2S)-2-(3-{[1-(2-Naphthoyl)-2-methyl-5-(trifluoromethoxy)-1H-indol-3-yl]methyl}phenoxy)propanoic acid;

2-(2-{[1-(4-Methoxybenzoyl)-2-methyl-5-(trifluoromethoxy)-1H-indol-3-yl]methyl}phenoxy)-2-methylpropanoic acid;

2-(3-{[1-(4-Methoxybenzoyl)-2-methyl-5-(trifluoromethoxy)-1H-indol-3-yl]methyl}phenoxy)-2-methylpropanoic acid;

2-(2-{[1-(2-Naphthoyl)-2-methyl-5-(trifluoromethoxy)-1H-indol-3-yl]methyl}phenoxy)-2-methylpropanoic acid;

2-(3-{[1-(2-Naphthoyl)-2-methyl-5-(trifluoromethoxy)-1H-indol-3-yl]methyl}phenoxy)-2-methylpropanoic acid;

(2R)-2-(3-{2-[1-(4-Methoxybenzoyl)-2-methyl-5-(trifluoromethoxy)-1H-indol-3-yl]ethyl}phenoxy)propionic acid;

(2S)-2-{3-[1-(4-methoxybenzoyl)-2-methyl-5-(trifluoromethoxy)-1H-indol-3-yl]phenoxy}propionic acid;

(2S)-2-(3-{1-{1-(4-Methoxybenzoyl)-2-methyl-5-(trifluoromethoxy)-1H-indol-3-yl]cyclopropyl}phenoxy)propanoic acid; and 2-{3-[1-(4-Methoxybenzoyl)-2-methyl-5-(trifluoromethoxy)-1H-indol-3-yl]phenoxy}-2-methylpropanoic acid.

17. A pharmaceutical composition comprising a compound of claim 1 and a pharmaceutically acceptable carrier.

18. A method for treating non-insulin dependent (Type 2) diabetes mellitus in a mammalian patient in need of such treatment which comprises administering to said patient a therapeutically effective amount of a compound of claim 1.

19. A method for treating hyperglycemia in a mammalian patient in need of such treatment which comprises administering to said patient a therapeutically effective amount of a compound of claim 1.

20. A method for treating lipid disorders, hyperlipidemia, and low HDL in a mammalian patient in need of such treatment which comprises administering to said patient a therapeutically effective amount of a compound of claim 1.

21. A method for treating obesity in a mammalian patient in need of such treatment which comprises administering to said patient a therapeutically effective amount of a compound of claim 1.

22. A method for treating hypercholesterolemia in a mammalian patient in need of such treatment which comprises administering to said patient a therapeutically effective amount of a compound of claim 1.

23. A method for treating hypertriglyceridemia in a mammalian patient in need of such treatment which comprises administering to said patient a therapeutically effective amount of a compound of claim 1.

24. A method for treating dyslipidemia and/or low HDL cholesterol in a mammalian patient in need of such treatment which comprises administering to said patient a therapeutically effective amount of a compound of claim 1.

25. A method for treating atherosclerosis in a mammalian patient in need of such treatment which comprises administering to said patient a therapeutically effective amount of a compound of claim 1.

26. A method of treating one or more diseases, disorders, or conditions selected from the group consisting of (1) non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis, (14) vascular restenosis, (15) irritable bowel syndrome, (16) inflammatory bowel disease, (17) Crohn's disease, (18) ulcerative colitis, (19) gout, (20) rheumatoid arthritis, (21) osteoarthritis, (22)multiple sclerosis, (23) asthma, (24) ARDS, (25) psoriasis, (26) vasculitis, (27) ischemia, (28) frostbite, (29) pancreatitis, (30) abdominal obesity, (31) neurodegenerative disease, (32) retinopathy, (33) Syndrome X, and (34) ovarian hyperandrogenism (polycystic ovarian syndrome), said method comprising the administration of an effective amount of a compound of claim 1.

27. A method of treating one or more diseases, disorders, or conditions selected from the group consisting of (1) diabetes mellitus, (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, ( 1) low HDL levels, (12) high LDL levels, (13) atherosclerosis, (14) vascular restenosis, (15) irritable bowel syndrome, (16) inflamatory bowel disease, (17) Crohn's disease, (18) ulcerative colitis, (19) gout, (20) rheumatoid arthritis, (21) osteoarthritis, (22)multiple sclerosis, (23) asthma, (24) ARDS, (25) psoriasis, (26) vasculitis, (27) ischemia, (28) frostbite, (29) pancreatitis, (30) abdominal obesity, (31) neurodegenerative disease, (32) retinopathy, (33) Syndrome X, and (34) ovarian hyperandrogenism (polycystic ovarian syndrome), said method comprising the administration of an effective amount of a compound of claim 1, and an effective amount of one or more other compounds selected from the group consisting of:

(a) other compounds that are used in the treatment of type 2 diabetes, selected from (i) PPAR agonists; (ii) biguanides; (iii) protein tyrosine phosphatase-1B (PTP-1B) inhibitors; and (iv) dipeptidyl peptidase IV (DP-IV) inhibitors;

(b) insulin or insulin mimetics;

(c) sulfonylureas;

(d) α-glucosidase inhibitors;

(e) cholesterol lowering agents selected from (i) HMG-CoA reductase inhibitors; (ii) sequestrants; (iii) nicotinyl alcohol, nicotinic acid or a salt thereof, (iv) PPARα agonists; (v) PPARα/γ dual agonists; (vi) inhibitors of cholesterol absorption; (vii) acyl CoA:cholesterol acyltransferase inhibitors; and (viii) anti-oxidants;

(f) PPARδ agonists;

(g) antiobesity compounds;

(h) an ileal bile acid transporter inhibitor; and (i) agents used in inflammatory conditions.

28. A method for the treatment of one or more conditions selected from hypercholesterolemia, atherosclerosis, low HDL levels, high LDL levels, hyperlipidemia, hypertriglyceridemia, and dyslipidemia, which method comprises administering to a mammalian patient in need of such treatment a therapeutically effective amount of a compound of claim 1.

29. A method for the treatment of one or more conditions selected from hypercholesterolemia, atherosclerosis, low HDL levels, high LDL levels, hyperlipidemia, hypertriglyceridemia, and dyslipidemia, which method comprises administering to a mammalian patient in need of such treatment a therapeutically effective amount of a combination of a compound of claim 1 and an HMG-CoA reductase inhibitor.

30. The method as recited in claim 29, wherein the HMG-CoA reductase inhibitor is a statin.

31. The method as recited in claim 30, wherein the statin is selected from the group consisting of lovastatin, simvastatin, pravastatin, fluvastatin, atorvastatin, itavastatin, ZD-4522 and rivastatin.

32. A method for the treatment of one or more conditions selected from inflammatory bowel disease, Crohn's disease, and ulcerative colitis, which method comprises administering to a mammalian patient in need of such treatment a therapeutically effective amount of a compound of claim 1.

33. A method for treating atherosclerosis in a mammalian patient in need of such treatment comprising the administration to said patient of an effective amount of a combination of a compound of claim 1 and an an HMG-CoA reductase inhibitor.

34. A pharmaceutical composition comprising: (1) a compound of claim 1, (2) an HMG-CoA reductase inhibitor, and (3) a pharmaceutically acceptable carrier.

35. A pharmaceutical composition comprising (1) a compound of claim 1, (2) one or more compounds selected from the group consisting of
   (a) other compounds that are used in the treatment of type 2 diabetes selected from (i) PPARγ agonists; (ii) biguanides; (iii) protein tyrosine phosphatase-1B (PTP-1B) inhibitors, and (iv) dipeptidyl peptidase IV (DP-IV) inhibitors;
   (b) insulin or insulin mimetics;
   (c) sulfonylureas;
   (d) α-glucosidase inhibitors;
   (e) cholesterol lowering agents selected from (i) HMG-CoA reductase inhibitors; (ii) sequestrants; (iii) nicotinyl alcohol, nicotinic acid or a salt thereof; (iv) PPARα agonists; (v) PPARα/γ dual agonists; (vi) inhibitors of cholesterol absorption;
   (vii) acyl CoA:cholesterol acyltransferase inhibitors; and (viii) anti-oxidants;
   (f) PPARδ agonists;
   (g) antiobesity compounds;
   (h) an ileal bile acid transporter inhibitor; and
   (i) agents used in inflammatory conditions; and (3) a pharmaceutically acceptable carrier.

36. A compound of formula I:

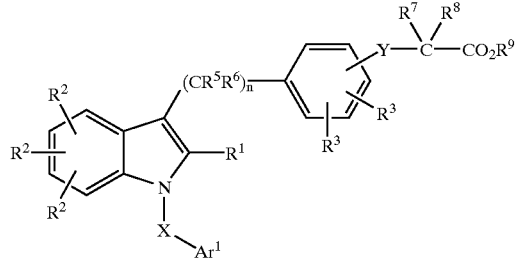

wherein:
   $R^1$ is methyl, optionally substituted with 1–3 F;
   $R^2$, $R^3$ and $R^4$ are each independently selected from the group consisting of H, halogen, $C_1$–$C_6$ alkyl, $C_2$–$C_6$ alkenyl, $C_2$–$C_6$ alkynyl, $C_3$–$C_8$ cycloalkyl, aryl, $OC_1$–$C_6$ alkyl, $OC_2$–$C_6$ alkenyl, $OC_2$–$C_6$ alkynyl, O-aryl, OH, $SC_1$–$C_6$ alkyl, $SC_2$–$C_6$ alkenyl, $SC_2$–$C_6$ alkynyl, $SO_2C_1$–$C_6$ alkyl, $SO_2C_2$–$C_6$ alkenyl, $SO_2C_2$–$C_6$ alkynyl, $OCON(R_5)_2$, $OCO(C_1$–$C_6$-alkyl) and CN, wherein all instances of alkyl, alkenyl and alkynyl are optionally linear or branched and all instances of alkyl, alkenyl, alkynyl, cycloalkyl and aryl are optionally substituted with 1–5 substituents independently selected from the group consisting of halogen, aryl, O-aryl and OMe;

$R^5$ and $R^6$ are, at each occurrence, independently selected from the group consisting of H, F, OH and C–$C_5$ alkyl, and $R^5$ and $R^6$ groups that are on the same carbon atom optionally may be joined to form a $C_3$–$C_6$ cycloalkyl group;

$R^7$ and $R^8$ are each independently selected from the group consisting of H, F, and $C_{1-5}$ alkyl, or $R^7$ and $R^8$ optionally may be joined to form a $C_3$–$C_6$ cycloalkyl group;

$OR^9$ of the group —$CO_2R^9$ is selected from the group consisting of —$OR^{10}$, —$OCH_2OR^{10}$, —$OCH(CH_3)OR^{10}$, —$OCH_2OC(O)R^{10}$, —$OCH(CH_3)OC(O)R^{10}$, —$OCH_2OC(O)OR^{10}$, —$OCH(CH_3)OC(O)OR^{10}$, —$NR^{11}R^{11}$, and —$ONR^{11}R^{11}$, wherein each $R^{10}$ is independently selected from $C_1$–$C_6$ alkyl optionally substituted with one or two groups selected from —$CO_2H$, —$CONH_2$, $NH_2$, —OH, —OAc, NHAc and phenyl; and wherein each $R^{11}$ is independently selected from H and $R^{10}$;

$Ar^1$ is phenyl, 1-naphthyl, 2-naphthyl, pyridyl or quinolyl wherein $Ar^1$ is substituted with 1–3 groups independently selected from $R^4$;

X is selected from the group consisting of C=O, $S(O)_2$, $CH_2$, $CH(CH_3)$, $C(CH_3)_2$, $CF_2$, and cyclopropylidene;

Y is O or S; and n is 0–5;

and pharmaceutically acceptable salts thereof.

37. A compound which is selected from the group consisting of:

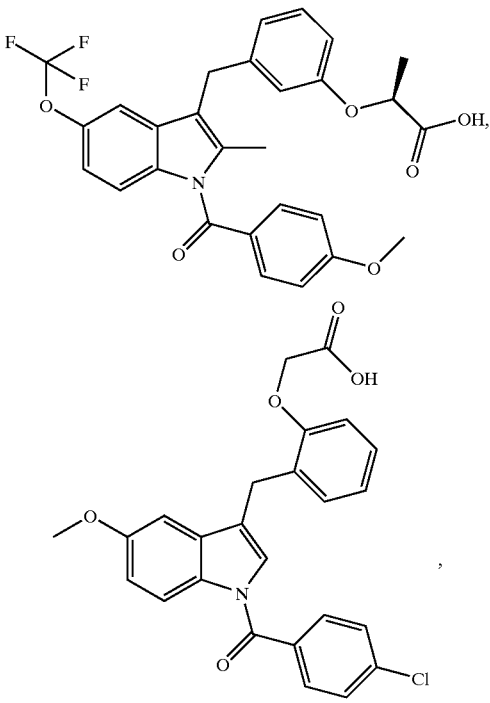

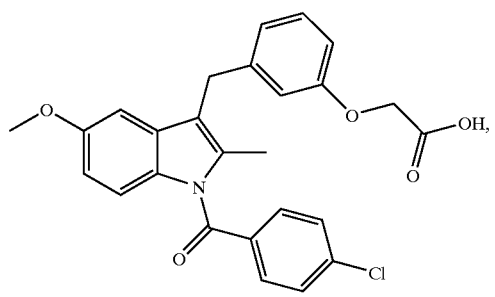
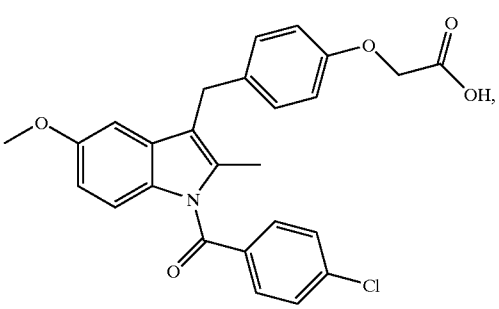
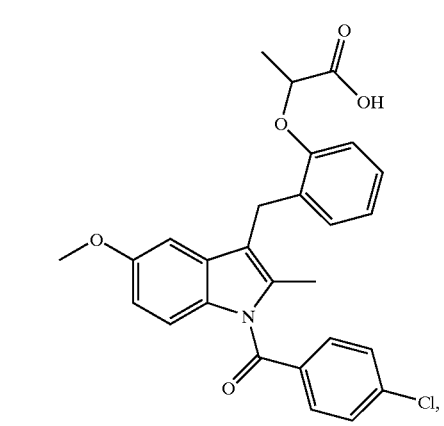
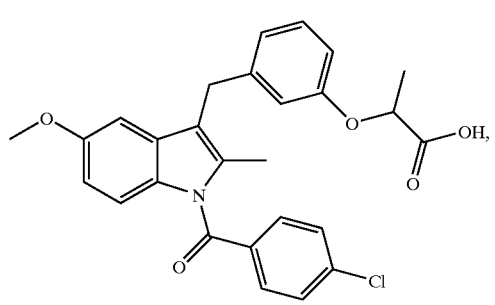
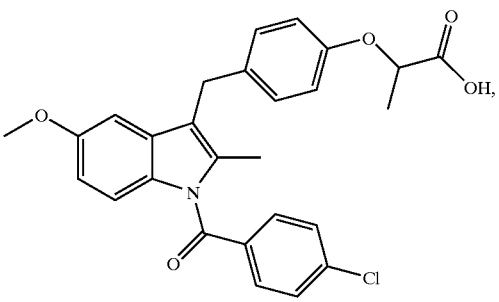
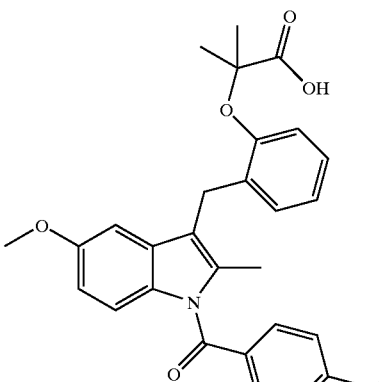
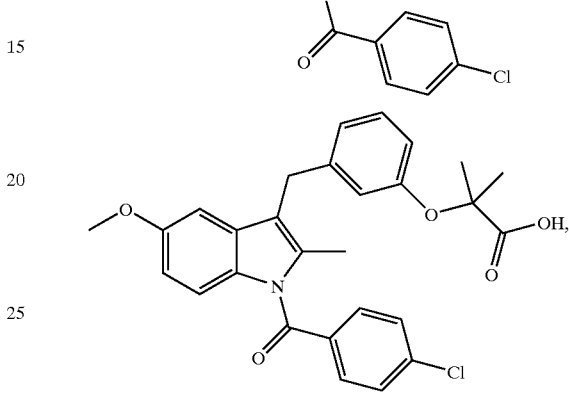
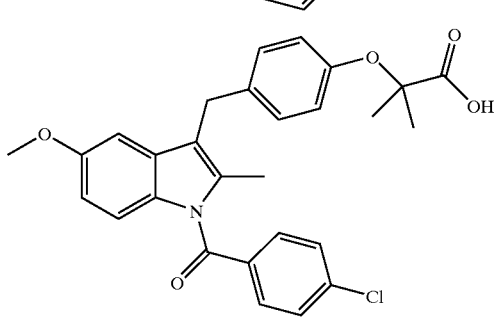
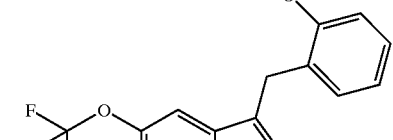
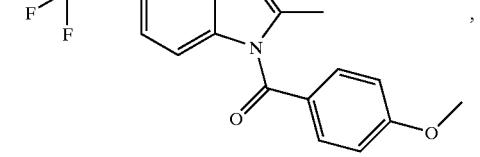
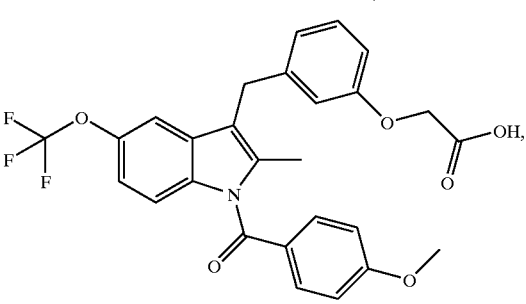

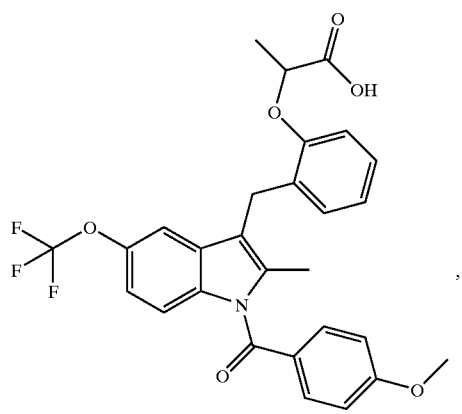,
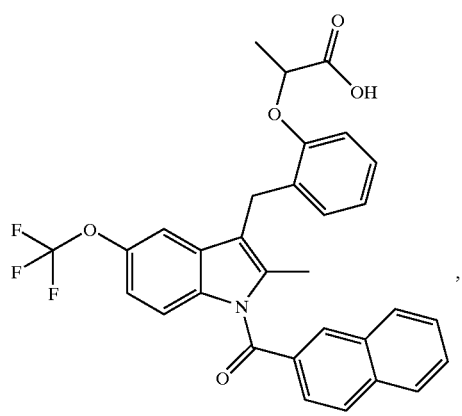,
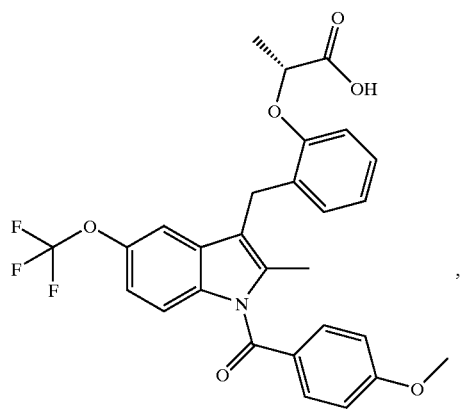,
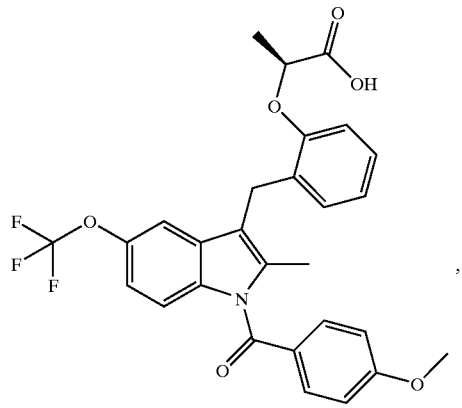,
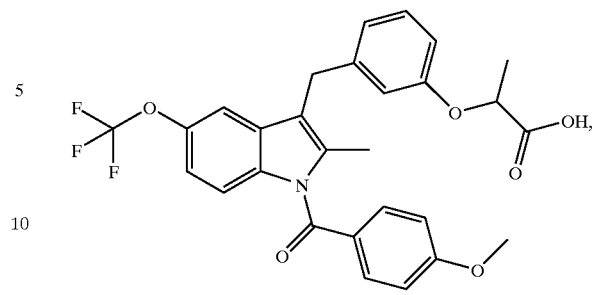,
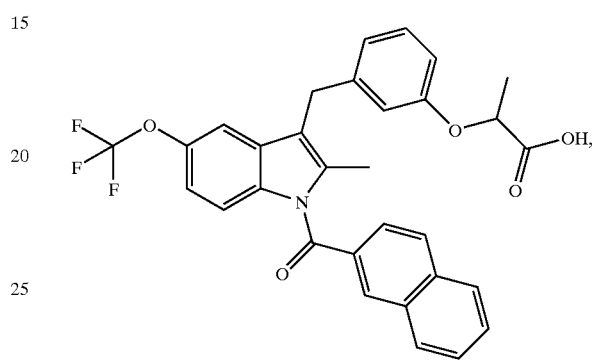,
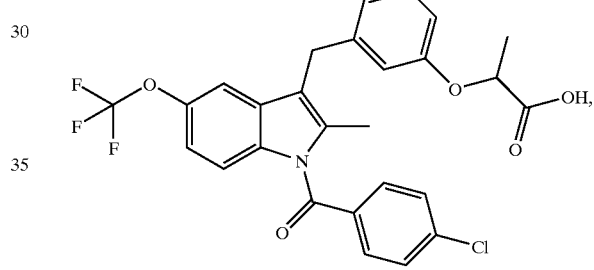,
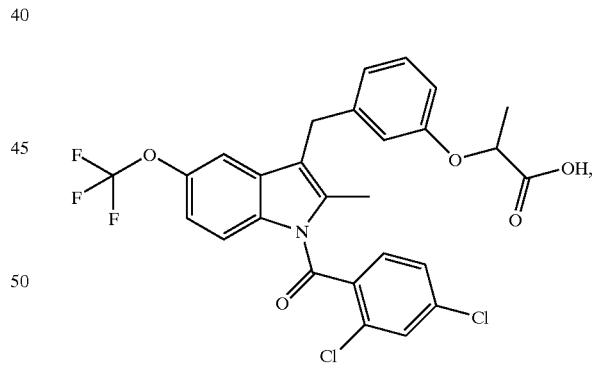,
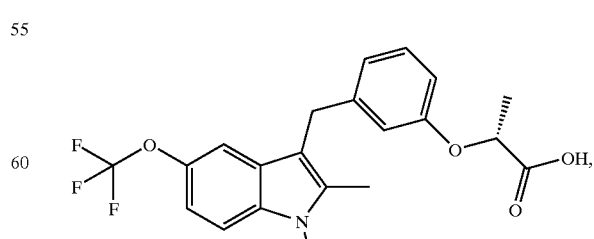, -continued
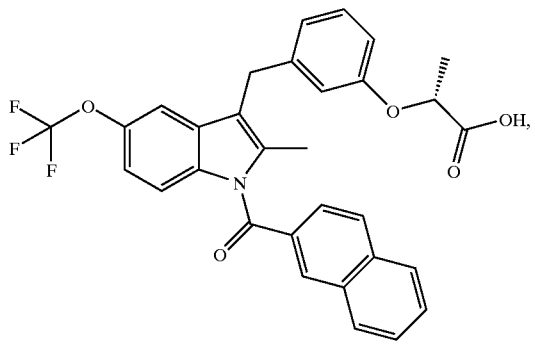
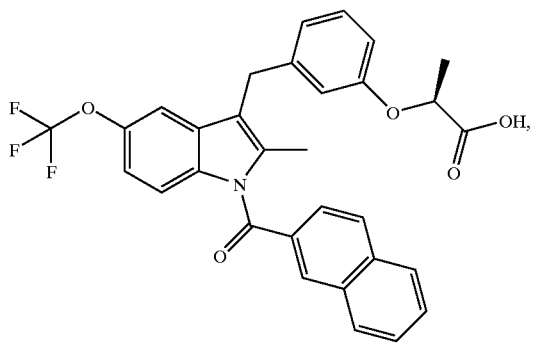
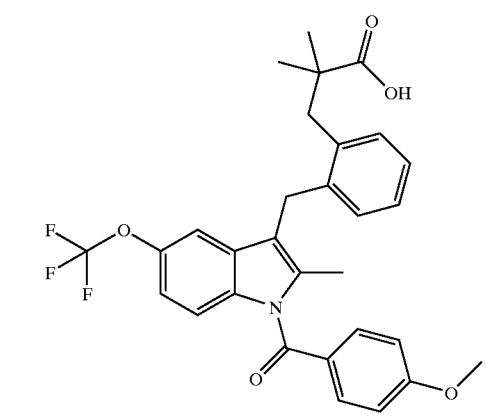
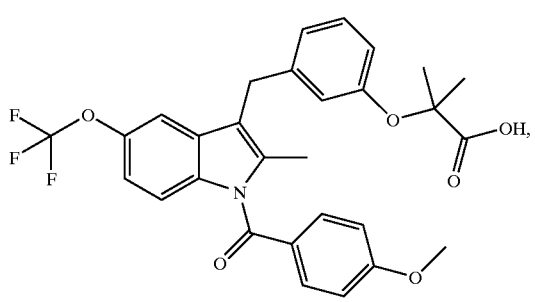
-continued
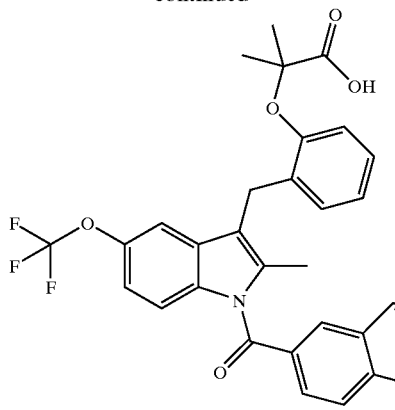
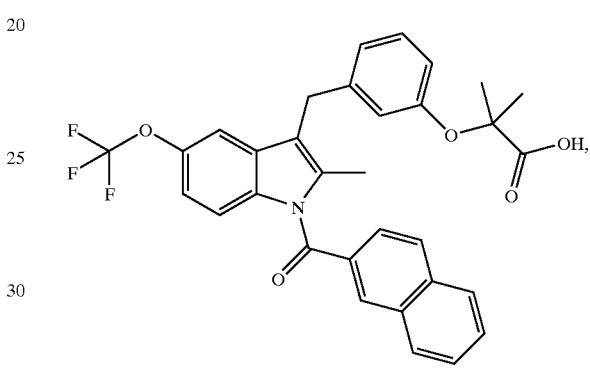
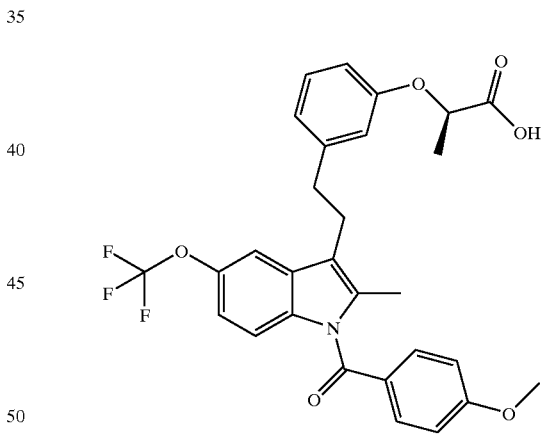
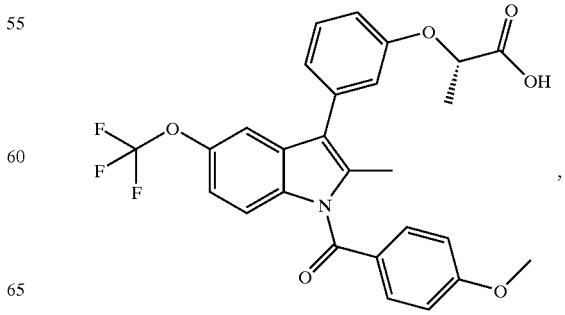

55
-continued
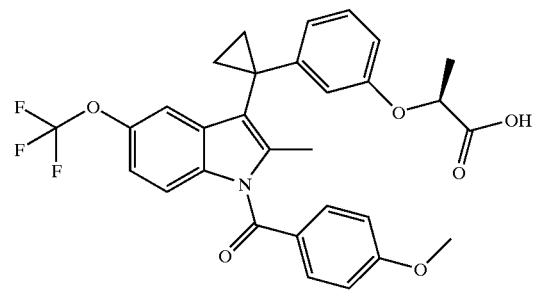
, and
56
-continued
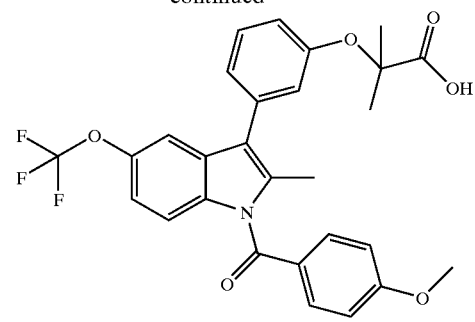
* * * * *